United States Patent
Nishide et al.

(10) Patent No.: US 12,226,077 B2
(45) Date of Patent: Feb. 18, 2025

(54) COMPUTER-READABLE MEDIUM CONTANING A PROGRAM, METHOD, AND APPARATUS FOR GENERATING A VIRTUAL ENDOSCOPIC IMAGE AND OUTPUTTING OPERATION ASSISTANCE INFORMATION

(71) Applicant: HOYA CORPORATION, Tokyo (JP)

(72) Inventors: Akihiko Nishide, Tokyo (JP); Junko Sugai, Kanagawa (JP)

(73) Assignee: HOYA CORPORATION, Tokyo (JP)

( * ) Notice: Subject to any disclaimer, the term of this patent is extended or adjusted under 35 U.S.C. 154(b) by 426 days.

(21) Appl. No.: 17/766,056

(22) PCT Filed: Jan. 28, 2021

(86) PCT No.: PCT/JP2021/002954
§ 371 (c)(1),
(2) Date: Apr. 1, 2022

(87) PCT Pub. No.: WO2021/192593
PCT Pub. Date: Sep. 30, 2021

(65) Prior Publication Data
US 2022/0351407 A1 Nov. 3, 2022

(30) Foreign Application Priority Data
Mar. 26, 2020 (JP) ................. 2020-056712

(51) Int. Cl.
*G06K 9/00* (2022.01)
*A61B 1/005* (2006.01)
*G06T 7/70* (2017.01)

(52) U.S. Cl.
CPC .............. *A61B 1/009* (2022.02); *A61B 1/005* (2013.01); *G06T 7/70* (2017.01);
(Continued)

(58) Field of Classification Search
CPC ......... G06T 2207/10068; G06T 7/0012; A61B 1/0005
See application file for complete search history.

(56) References Cited

U.S. PATENT DOCUMENTS

| 2005/0010082 A1 | 1/2005 | Nishimura et al. |
| 2009/0041320 A1 | 2/2009 | Tanaka |

(Continued)

FOREIGN PATENT DOCUMENTS

| JP | 2002-238887 | 8/2002 |
| JP | 2003-93328 | 4/2003 |

(Continued)

OTHER PUBLICATIONS

International Search Report issued in International Bureau of WIPO Patent Application No. PCT/JP2021/002954, dated Apr. 20, 2021, along with an English translation thereof.

*Primary Examiner* — Gregory A Morse
*Assistant Examiner* — Owais Iqbal Memon
(74) *Attorney, Agent, or Firm* — GREENBLUM & BERNSTEIN, P.L.C.

(57) ABSTRACT

There is provided a program causing a computer to execute processing including: acquiring an endoscopic image of a subject from an endoscope; acquiring a three-dimensional medical image obtained by capturing an image of an internal body portion of the subject by means of X-ray CT, X-ray cone beam CT, MRI-CT, or an ultrasonic diagnosis apparatus configured to capture a three-dimensional image of an internal body portion of the subject; generating a virtual endoscopic image reconfigured from the three-dimensional medical image, based on the acquired endoscopic image; calculating distance image information in the endoscopic image based on the virtual endoscopic image and the endoscopic image; and outputting operation assistance informa- (Continued)

tion on an operation of the endoscope based on the distance image information and the three-dimensional medical image.

10 Claims, 15 Drawing Sheets

(52) U.S. Cl.
CPC ............... *G06T 2207/10068* (2013.01); *G06T 2207/10081* (2013.01); *G06T 2207/10132* (2013.01)

(56) References Cited

U.S. PATENT DOCUMENTS

| | | | | |
|---|---|---|---|---|
| 2009/0292175 | A1* | 11/2009 | Akimoto | A61B 1/2676 382/128 |
| 2012/0287238 | A1* | 11/2012 | Onishi | A61B 1/0005 348/45 |
| 2014/0088357 | A1* | 3/2014 | Ikuma | A61B 1/00009 600/109 |
| 2020/0078103 | A1 | 3/2020 | Duindam et al. | |
| 2023/0138666 | A1* | 5/2023 | Husta | A61B 6/12 600/117 |

FOREIGN PATENT DOCUMENTS

| | | |
|---|---|---|
| JP | 2007-282857 | 11/2007 |
| WO | 2012/101888 | 8/2012 |

* cited by examiner

COMPUTER-READABLE MEDIUM CONTANING A PROGRAM, METHOD, AND APPARATUS FOR GENERATING A VIRTUAL ENDOSCOPIC IMAGE AND OUTPUTTING OPERATION ASSISTANCE INFORMATION

TECHNICAL FIELD

The present technology relates to a program, an information processing method, an information processing apparatus, and a diagnosis assistance system.

The present application claims priority based on Japanese Patent Application No. 2020-056712 filed on Mar. 26, 2020,the entire contents of which are incorporated herein by reference.

BACKGROUND ART

In a tumor examination of a patient, an endoscope is inserted into a tubular organ portion such as the trachea and the bronchus, the upper gastrointestinal tract, the pancreas, the biliary tract, or the intestinal tract, and the examination is mostly performed based on an image from the inserted endoscope. However, in two-dimensional image information of an endoscopic image, a distance to each pixel is not known, a geometric distortion of the image occurs, and an error in image measurement is large. As a result, it is difficult to provide image diagnosis support information by using only an endoscopic image. On the other hand, a virtual endoscope disclosed in Patent Literature 1 provides a virtual endoscopic image using data of an X-ray computed tomography (CT) image. The virtual endoscopic image is created from a three-dimensional X-ray CT image.

CITATION LIST

Patent literature

Patent Literature 1: IP 2002-238887 A

SUMMARY OF INVENTION

Technical Problem

However, the virtual endoscope disclosed in Patent Literature 1 merely displays an X-ray CT reconfigured cross-section image (virtual endoscopic image), and assisting diagnosis by providing information on an operation of the endoscope based on the endoscopic image and the virtual endoscopic image is not taken into account.

In one aspect, an object is to provide a program and the like that perform efficient diagnosis assistance by providing information on an operation of an endoscope.

Solution to Problem

According to an aspect of the present disclosure, there is provided a program causing a computer to execute processing including: acquiring an endoscopic image of a subject from an endoscope; acquiring a three-dimensional medical image obtained by capturing an image of an internal body portion of the subject by means of X-ray CT, X-ray cone beam CT, MRI-CT or an ultrasonic diagnosis apparatus configured to capture a three-dimensional image of an internal body portion of the subject; generating a virtual endoscopic image reconfigured from the three-dimensional medical image, based on the acquired endoscopic image; calculating distance image information in the endoscopic image based on the virtual endoscopic image and the endoscopic image; and outputting operation assistance information on an operation of the endoscope based on the distance image information and the three-dimensional medical image.

According to another aspect of the present disclosure, there is provided an information processing method causing a computer to execute processing including: acquiring an endoscopic image of a subject from an endoscope; acquiring a three-dimensional medical image obtained by capturing an image of an internal body portion of the subject by means of X-ray CT, X-ray cone beam CT, MRI-CT, or an ultrasonic diagnosis apparatus configured to capture a three-dimensional image of an internal body portion of the subject; generating a virtual endoscopic image reconfigured from the three-dimensional medical image, based on the acquired endoscopic image; calculating distance image information in the endoscopic image based on the virtual endoscopic image and the endoscopic image; and outputting operation assistance information on an operation of the endoscope based on the distance image information and the three-dimensional medical image.

According to still another aspect of the present disclosure, there is provided an information processing apparatus including: an endoscopic image acquisition unit that acquires an endoscopic image of a subject from an endoscope; a three-dimensional medical image acquisition unit that acquires a three-dimensional medical image obtained by capturing an image of an internal body portion of the subject by means of X-ray CT, X-ray cone beam CT, MRI-CT, or an ultrasonic diagnosis apparatus configured to capture a three-dimensional image of an internal body portion of the subject; a generation unit that generates a virtual endoscopic image reconfigured from the three-dimensional medical image, based on the acquired endoscopic image; a calculation unit that calculates distance image information in the endoscopic image based on the virtual endoscopic image and the endoscopic image; and an output unit that outputs operation assistance information on an operation of the endoscope based on the distance image information and the three-dimensional medical image.

According to still another aspect of the present disclosure, there is provided a diagnosis assistance system including: an endoscope; an automatic operation mechanism that performs an automatic operation of the endoscope; and an endoscope processor that acquires an endoscopic image of a subject from the endoscope, in which the endoscope processor includes a three-dimensional medical image acquisition unit that acquires a three-dimensional medical image obtained by capturing an image of an internal both portion of the subject by means of X-ray CT, X-ray cone beam CT, WU-CT, or an ultrasonic diagnosis apparatus configured to capture a three-dimensional image of an internal body portion of the subject, a generation unit that generates a virtual endoscopic image reconfigured from the three-dimensional medical image, based on the acquired endoscopic image, a calculation unit that calculates distance image information in the endoscopic image based on the virtual endoscopic image and the endoscopic image, and an output unit that outputs operation assistance information on an operation of the endoscope to the automatic operation mechanism based on the distance image information and the three-dimensional medical image, and in which the automatic operation mechanism performs an automatic operation of the endoscope according to the operation assistance information output from the output unit.

Advantageous Effects of invention

According to the present disclosure, it is possible to provide a program and the like that perform efficient diagnosis assistance by providing information on an operation of the endoscope.

DESCRIPTION OF EMBODIMENTS

First Embodiment

Figure 1:
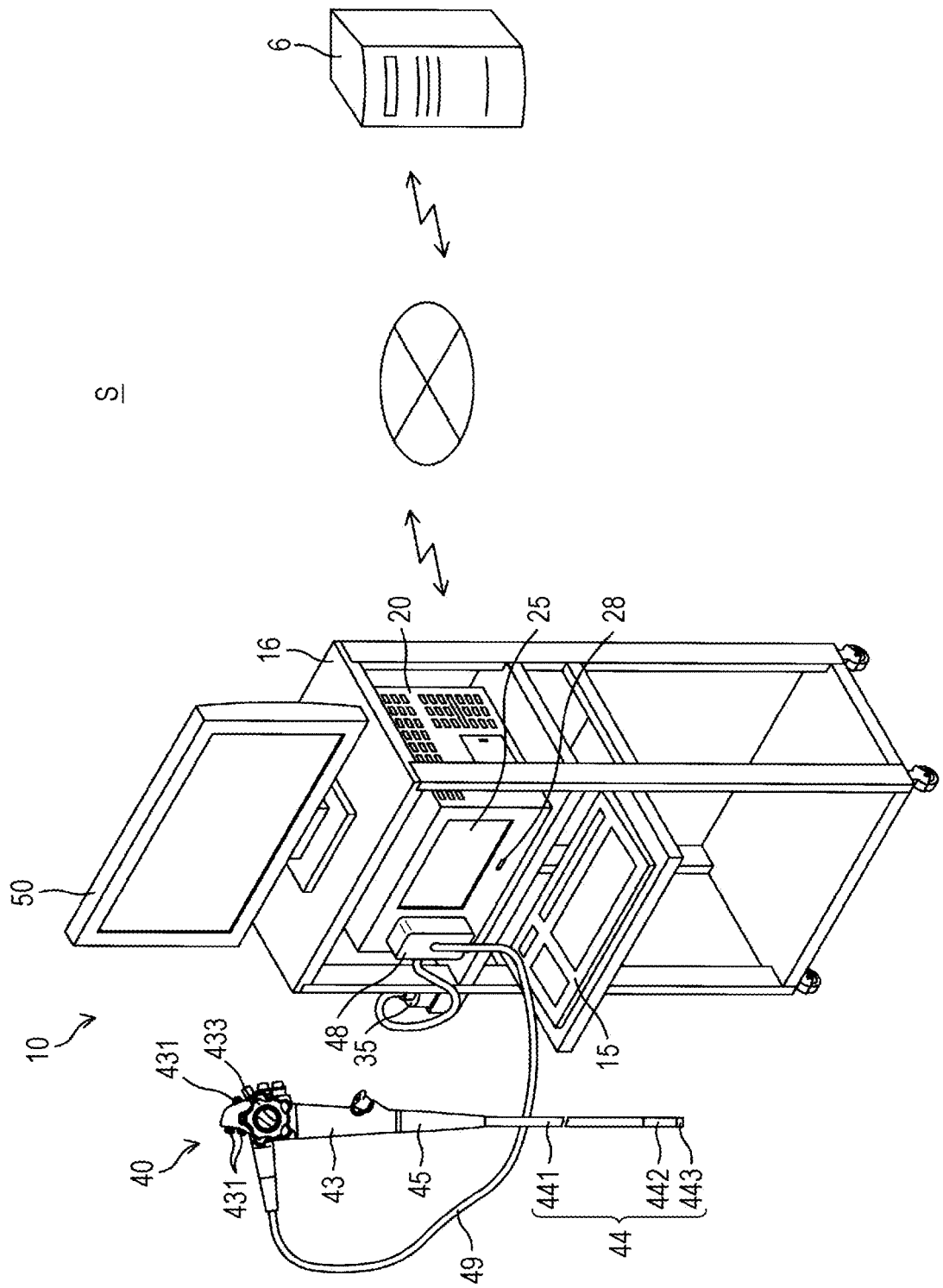
FIG. 1 is a schematic diagram illustrating an outline of a diagnosis assistance system according to a first embodiment.

Hereinafter, the present invention will be specifically described with reference to the drawings illustrating embodiments of the present invention. FIG. 1 is a schematic diagram illustrating an outline of a diagnosis assistance system S according to a first embodiment. The diagnosis assistance system S includes an endoscope apparatus 10 and an information processing apparatus 6 communicatively connected to the endoscope apparatus 10.

The endoscope apparatus 10 transmits an image (captured image) captured by an image sensor of an endoscope 40 to an endoscope processor 20, and the endoscope processor 20 performs various types of image processing such as gamma correction, white balance correction, and shading correction. Thereby, an endoscopic image easily observed by an operator is generated. The endoscope apparatus 10 outputs (transmits) the generated endoscopic image to the information processing apparatus 6. In a case where the information processing apparatus 6 acquires the endoscopic image transmitted from the endoscope apparatus 10, the information processing apparatus 6 performs various types of information processing based on these endoscopic images and outputs information on diagnosis assistance.

The endoscope apparatus 10 includes the endoscope processor 20, the endoscope 40, and a display device 50. The display device 50 is, for example, a liquid crystal display device or an organic electro luminescence (EL) display device.

The display device 50 is provided on an upper stage of a storage shelf 16 with casters. The endoscope processor 20 is accommodated in a middle stage of the storage shelf 16. The storage shelf 16 is disposed in the vicinity of a bed for an endoscopic examination (not illustrated). The storage shelf 16 includes a drawer type shelf on which a keyboard 15 connected to the endoscope processor 20 is provided.

The endoscope processor 20 has a substantially rectangular parallelepiped shape and is provided with a touch panel 25 on one surface. A reading unit 28 is disposed at a bottom portion of the touch panel 25. The reading unit 28 is a connection interface for performing reading and writing on a portable recording medium such as a universal serial bus (USB) connector, a secure digital (SD) card slot, a compact disc read only memory (CD-ROM) drive, or the like.

The endoscope 40 includes an insertion portion 44, an operation unit 43, a universal cord 49, and a scope connector 48. The operation unit 43 is provided with a control button 431. The insertion portion 44 is long and has one end connected to the operation unit 43 via a bend preventing portion 45. The insertion portion 44 includes a soft portion 441, a bending portion 442, and a distal end portion 443 in order from a side of the operation unit 43. The bending portion 442 is bent according to an operation of a bending knob 433. Physical detection devices such as a three-axis acceleration sensor, a gyro sensor, a geomagnetic sensor, a magnetic coil sensor, and an endoscope-insertion-type observation device (colonoscope navigation) may be provided on the insertion portion 44. In a case where the endoscope 40 is inserted into a body of a subject, detection results from these physical detection devices may be acquired.

The universal cord 49 is long and has a first end connected to the operation unit 43 and a second end connected to the scope connector 48. The universal cord 49 is soft. The scope connector 48 has a substantially rectangular parallelepiped shape. The scope connector 48 is provided with an air supply/water supply port 36 (refer to FIG. 2) for connecting an air supply/water supply tube.

Figure 2:
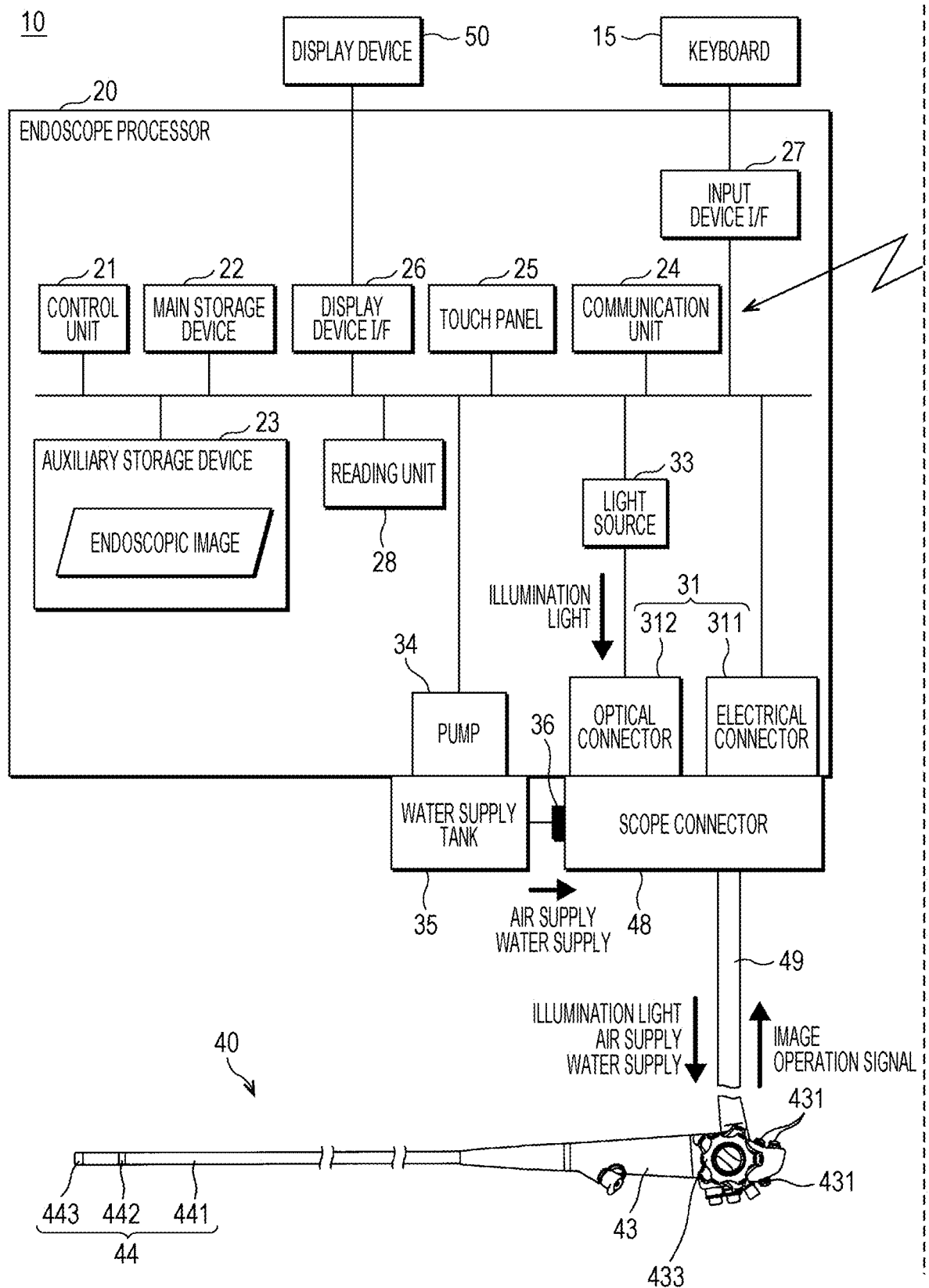
FIG. 2 is a block diagram illustrating a configuration example of an endoscope apparatus included in the diagnosis assistance system.

FIG. 2 is a block diagram illustrating a configuration example of the endoscope apparatus 10 included in the diagnosis assistance system S. A control unit 21 is an arithmetic control device that executes a program according to the present embodiment. One or a plurality of central processing units (CPUs), graphics processing units (GPUs), multi-core CPUs, or the like is used for the control unit 21. The control unit 21 is connected to each hardware unit of the endoscope processor 20 via a bus.

A main storage device 22 is, for example, a storage device such as a static random access memory (SRAM), a dynamic random access memory (DRAM), or a flash memory. The main storage device 22 temporarily stores information required in the middle of processing performed by the control unit 21 and a program being executed by the control unit 21. An auxiliary storage device 23 is, for example, a storage device such as an SRAM, a flash memory, or a hard disk and is a storage device having a capacity larger than that of the main storage device 22. In the auxiliary storage device 23, for example, the acquired captured image and the generated endoscopic image may be stored as intermediate data.

A communication unit 24 is a communication module or a communication interface for performing communication with the information processing apparatus 6 via a network in a wired or wireless manner and is, for example, a narrow-area wireless communication module such as Wi-Fi (registered trademark) or Bluetooth (registered trademark) or a wide-area wireless communication module such as 4G or Long Term Evolution (LTE). The touch panel 25 includes a display unit such as a liquid crystal display panel and an input unit layered on the display unit. The communication unit 24 may perform communication with a CT apparatus, an MRI apparatus (refer to FIG. 5), an ultrasonic diagnosis apparatus, or a storage device (not illustrated) that stores data output from these apparatuses.

A display device I/F 26 is an interface for connecting the endoscope processor 20 and the display device 50. An input device I/F 27 is an interface for connecting the endoscope processor 20 and an input device such as the keyboard 15.

A light source 33 is a high-luminance white light source such as a white LED or a xenon lamp. The light source 33 is connected to the bus via a driver (not illustrated). In the light source 33, turning on, fuming off, and a change of luminance are controlled by the control unit 21. Illumination light emitted from the light source 33 is incident on an optical connector 312. The optical connector 312 engages with the scope connector 48 to supply the illumination light to the endoscope 40.

A pump 34 generates a pressure for the air supply and water supply function of the endoscope 40. The pump 34 is connected to the bus via a driver (not illustrated). In the pump 34, turning on, turning off, and a change of the pressure are controlled by the control unit 21. The pump 34 is connected to the air supply/water supply port 36 provided in the scope connector 48 via a water supply tank 35.

An outline of functions of the endoscope 40 connected to the endoscope processor 20 will be described. A fiber bundle, a cable bundle, an air supply tube, a water supply tube, and the like are inserted inside the scope connector 48, the universal cord 49, the operation unit 43, and the insertion portion 44. The illumination light emitted from the light source 33 is emitted from an illumination window provided at the distal end portion 443 via the optical connector 312 and the fiber bundle. The image sensor provided at the distal end portion 443 captures an image of a range illuminated by the illumination light. The captured image is transmitted from the image sensor to the endoscope processor 20 via the cable bundle and an electrical connector 311.

The control unit 21 of the endoscope processor 20 functions as an image processing unit 211 by executing a program stored in the main storage device 22. The image processing unit 211 performs various types of image processing such as gamma correction, white balance correction, and shading correction on the image (captured image) output from the endoscope 40 and outputs the image as the endoscopic image.

Figure 3:
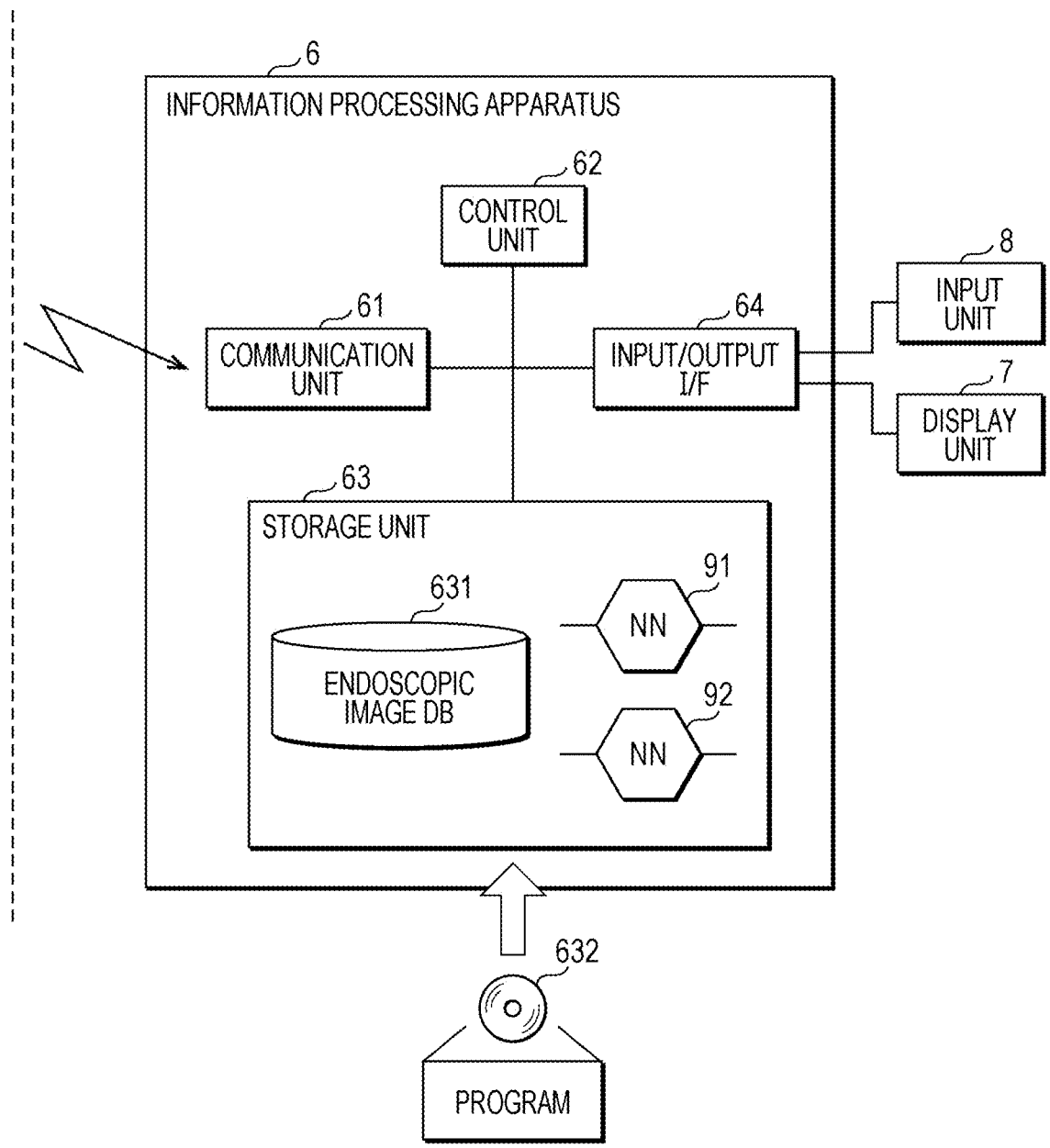
FIG. 3 is a block diagram illustrating a configuration example of an information processing apparatus included in the diagnosis assistance system.

FIG. 3 is a block diagram illustrating a configuration example of the information processing apparatus 6 included in the diagnosis assistance system S. The information processing apparatus 6 includes a control unit 62, a communication unit 61, a storage unit 63, and an input/output I/F 64. The information processing apparatus 6 is, for example, a server apparatus, a personal computer, or the like. The server apparatus includes not only a single server apparatus but also a cloud server apparatus or a virtual server apparatus including a plurality of computers. The information processing apparatus 6 may be provided as a cloud server located on an external network accessible from the endoscope processor 20.

The control unit 62 includes one or a plurality of arithmetic processing devices having a time counting function, such as central processing units (CPUs), micro-processing units (MPUs), and graphics processing units (CPUs), and performs various types of information processing, control processing, and the like related to the information processing apparatus 6 by reading and executing a program P stored in the storage unit 63. Alternatively, the control unit 62 may include a quantum computer chip, and the information processing apparatus 6 may be a quantum computer.

The storage unit 63 includes a volatile storage area such as a static random access memory (SRAM), a dynamic random access memory (DRAM), or a flash memory and a nonvolatile storage area such as an EEPROM or a hard disk. The storage unit 63 stores in advance the program P and data to be referred to at the time of processing. The program P stored in the storage unit 63 may he a program P which is read from a. recording medium 632 readable by the information processing apparatus 6. In addition, the program P may be a program which is downloaded from an external computer (not illustrated) connected to a communication network (not illustrated) and is stored in the storage unit 63. The storage unit 63 stores an entity file (instance file of a neural network (NN)) constituting each of a plurality of learning models (91 and 92) to be described later. These entity files may be configured as a part of the program P. Further, the storage unit 63 may store an endoscopic image database (DB) 631 to be described later.

The communication unit 61 is a communication module or a communication interface for performing communication with the endoscope apparatus 10 in a wired or wireless manner and is, for example, a narrow-area wireless communication module such as Wi-Fi (registered trademark) or Bluetooth (registered trademark) or a wide-area wireless communication module such as 4G or LTE. The communication unit 61 may perform communication with a CT apparatus, an MR1 apparatus (refer to FIG. 5), an ultrasonic diagnosis apparatus, or a storage device (not illustrated) that stores data output from these apparatuses.

The input/output I/F 64 is a communication interface conforming, for example, to a communication standard such as USB or DSUB and is a communication interface for performing serial communication with an external apparatus connected to the input/output I/F 64. For example, a display unit 7 such as a display and an input unit 8 such as a keyboard are connected to the input/output I/F 64, and the control unit 62 outputs, to the display unit 7, a result of information processing performed based on an execution command or an event input from the input unit 8.

Figure 4:
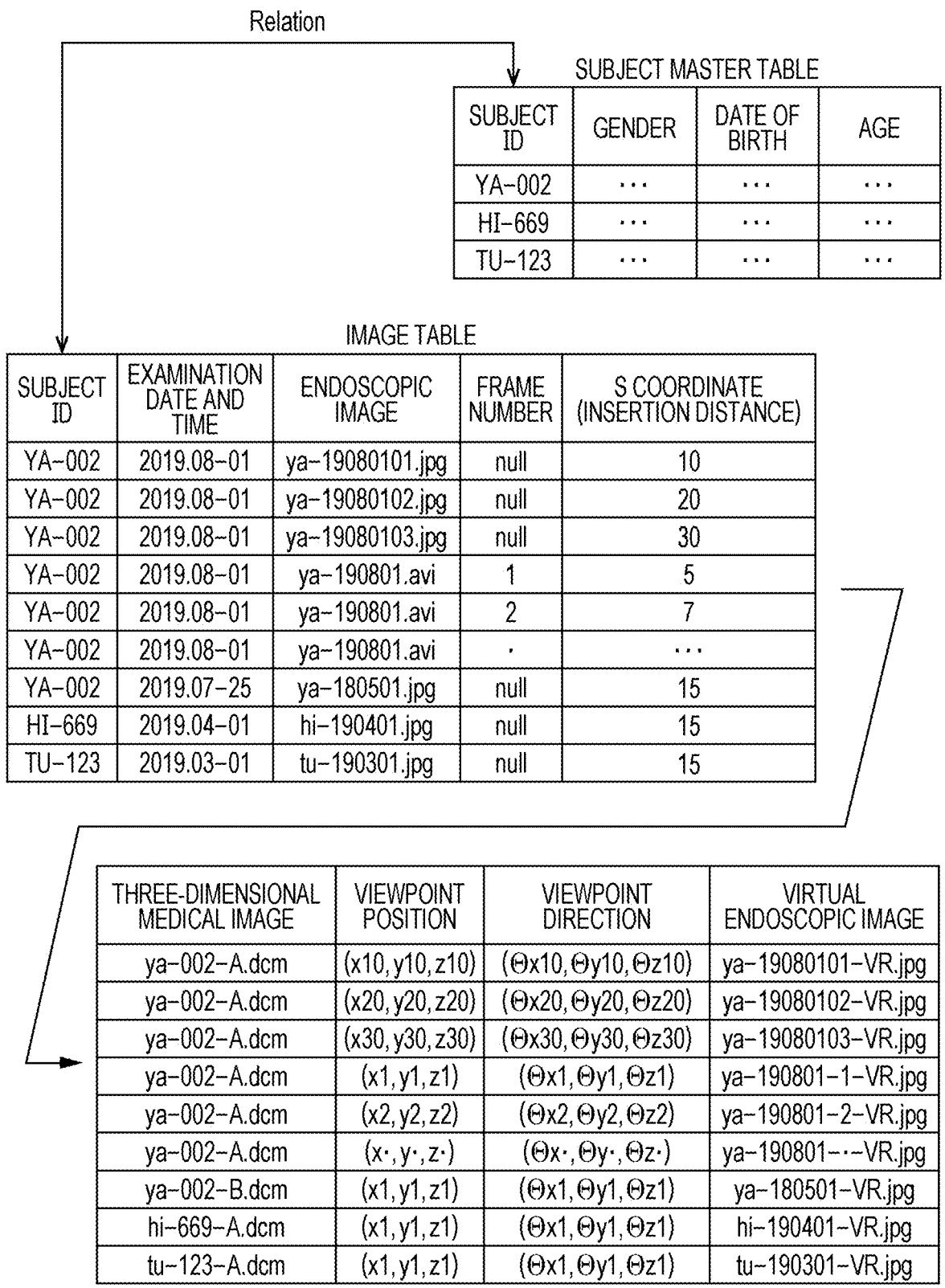
FIG. 4 is an explanatory diagram exemplifying a data layout of an endoscopic image DB.

FIG. 4 is an explanatory diagram exempl4ing a data layout of the endoscopic image DB 631. The endoscopic image DB 631 is stored in the storage unit 63 of the information processing apparatus 6, and is configured by database management software such as a relational database management system (RDBMS) implemented in the information processing apparatus 6. Alternatively, the endoscopic image DB 631 may be stored in a predetermined storage area accessible from the information processing apparatus 6, such as a storage device which is communicatively connected to the information processing apparatus 6. Alternatively, the endoscopic image DB 631 may be stored in the main storage device 22 of the endoscope apparatus 10. That is, the predetermined storage area includes the storage unit 63 of the information processing apparatus 6, the main storage device 22 of the endoscope apparatus 10, and a storage device accessible from the information processing apparatus 6 or the endoscope apparatus 10. The information processing apparatus 6 may acquire the endoscopic image which is output by the endoscope processor 20, an examination date and time, and attribute information of the subject, and register the acquired endoscopic image, the acquired examination date and time, and the acquired attribute information of the subject in the endoscopic image DB 631. Alternatively, the endoscopic image which is directly output from the endoscope processor 20, the examination date and time, and the attribute information of the subject may be directly registered in the endoscopic image DB 631.

The endoscopic image DB 631 includes, for example, a subject master table and an image table, and the subject master table and the image table are set to be associated with each other by a subject ID that is a common item (metadata) included in both the tables.

The subject master table includes, for example, the subject ID, a gender; a date of birth, and an age as management items (metadata). In the item (field) of the subject ID, ID information is stored in order to uniquely specify the subject who has an endoscopic examination. In the items (fields) of the gender and the date of birth, biological attributes including the gender and the date of birth corresponding to the subject ID are stored. In the item (field) of the age, the age at a current time calculated based on the date of birth is stored. The gender and the age are managed as biological information of the subject by the subject master table.

The image table includes, for example, as management items (metadata), a subject ID, an examination date and time, an endoscopic image, a frame number, an S coordinate (insertion distance), a three-dimensional medical image, a viewpoint position, a viewpoint direction, and a virtual endoscopic image.

In the item (field) of the subject ID, a value of the subject ID that is associated with the biological attribute of the subject managed in the subject master table is stored. In the item (field) of the examination date and time, a date and time when the subject corresponding to the subject ID has the endoscopic examination is stored. In the item (field) of the endoscopic image, the endoscopic image corresponding to the subject ID is stored as object data. The endoscopic image may be a still image in, tier example, a jpeg format with one frame or a moving image in, for example, an avi format with several frames. In the item (field) of the endoscopic image, information indicating a storage location (file path) of the endoscopic image stored as a file may be stored.

In a case where the endoscopic image is a moving image, in the item (field) of the frame number, the frame number of the moving image is stored. Even in a case where the endoscopic image is a moving image, by storing the frame number of the moving image, the moving image can be handled in the same manner as a still image, and can be associated with position information (a coordinate in an internal body coordinate system) of a three-dimensional medical image or a virtual endoscopic image to be described later.

In the item (field) of the S coordinate (insertion distance), the insertion distance of the endoscope 40 at the time of capturing the endoscopic image to be stored in the same record is stored as a value of the S coordinate. Calculation of the insertion distance (S coordinate) be described later.

In the item (field) of the three-dimensional medical image, for example, a three-dimensional medical image in a digital imaging and communications in medicine (DICOM) format is stored as object data, the three-dimensional medical image being generated based on data output from means configured to capture a three-dimensional image of an internal portion of the body, such as a CT apparatus (X-ray CT, X-ray cone beam CT), an MRI apparatus (MRI-CT), or an ultrasonic diagnosis apparatus. Alternatively, in the item (field) of the three-dimensional medical image, information indicating a storage location (file path) of the three-dimensional medical image stored as a file may he stored.

In the item (field) of the viewpoint position, a coordinate of the endoscope 40 in the body at the time of capturing the endoscopic image, that is, a coordinate in a coordinate system of the three-dimensional medical image is stored. Calculation of the viewpoint position will be described later.

In the item (field) of the viewpoint direction, a direction of the endoscope 40 at the time of capturing the endoscopic image, that is, a rotation angle in a coordinate system (a coordinate in the internal body coordinate system) of the three-dimensional medical image is stored. Calculation of the viewpoint direction will be described later.

In the item (field) of the virtual endoscopic image, the virtual endoscopic image generated from the three-dimensional medical image is stored as object data. In the item (field) of the virtual endoscopic image, information indicating a storage location (file path) of the virtual endoscopic image stored as a file may be stored. The virtual endoscopic image is generated from the three-dimensional medical image in order to perform matching processing with the endoscopic image. For example, a virtual endoscopic image having a highest matching degree with the endoscopic image is registered in the same record as the endoscopic image. Generation of the virtual endoscopic image will be described later.

Figure 5:
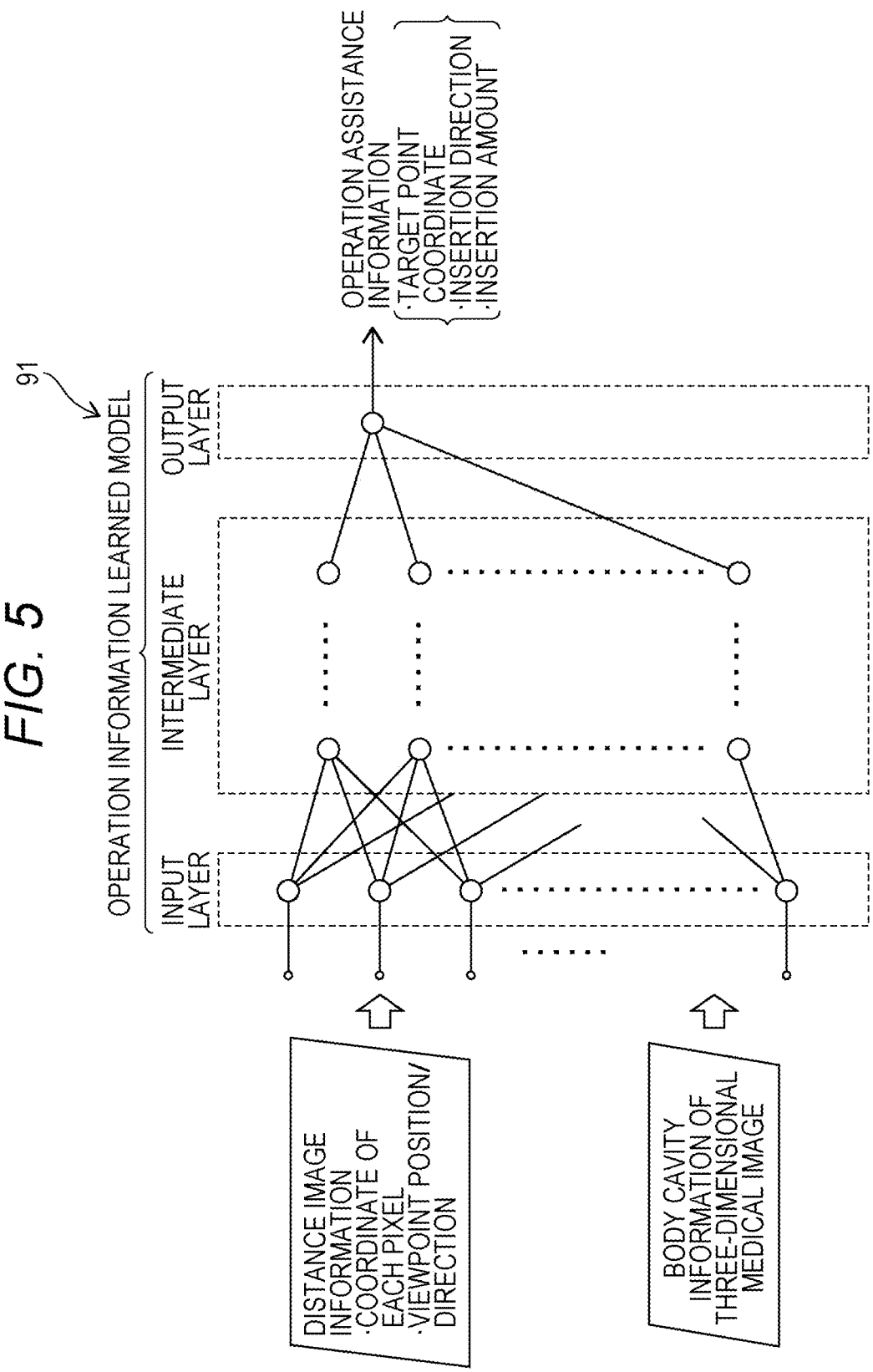
FIG. 5 is an explanatory diagram for explaining processing of outputting operation assistance information using an operation information learning model.

FIG. 5 is an explanatory diagram for explaining processing of outputting operation assistance information using an operation information learning model 91. The information processing apparatus 6 configures (generates) a neural network (operation information learning model 91) that receives distance image information and a three-dimensional medical image and outputs operation assistance information including an insertion direction of the endoscope 40, by performing learning based on training data. by setting, as inquiry data, distance image information to be described later and body cavity information included in a three-dimensional medical image and setting, as answer data, operation assistance information including at least one of an insertion direction, an insertion amount, and an insertion speed of the endoscope 40, and a target point coordinate indicating an insertion destination of the endoscope 40.

It is assumed that the operation information learning model 91 learned using the training data is used as a program module which is a part of artificial intelligence software. The operation information learning model 91 is used in the information processing apparatus 6 including the control unit 62 (CPU or the like) and the storage unit 63 as described above, and is executed. by the information processing apparatus 6 having arithmetic processing capability. Thereby, a neural network system is configured. That is, the control unit 62 of the information processing apparatus 6 operates to perform an arithmetic operation of extracting feature amounts of the distance image information and the three-dimensional medical image, which are input into an input layer, according to a command. from the operation information learning model 91 stored in the storage unit 63 and output the operation assistance information including the insertion direction of the endoscope 40 from an output layer.

The input layer includes a plurality of neurons that receive the distance image information and the body cavity information included in the three-dimensional medical image and transfer the input distance image information and the input body cavity information included in the three-dimensional medical image to an intermediate layer. Although described in detail later, the distance image information is information calculated based on a virtual endoscopic image corresponding to the acquired endoscopic image, and is information on a distance between pixels in the virtual endoscopic image. Since the endoscopic image and the corresponding virtual endoscopic image include, as an imaging region, a region of the same internal body part, the distance image information corresponds to information on the distance between pixels in the endoscopic image. The distance between pixels means a distance in the coordinate system (internal body coordinate system) of the three-dimensional medical image, and is, for example, a distance in consideration of a depth in two internal body parts included in the virtual endoscopic image. Further, information on the viewpoint position and the direction of the endoscope 40 may be reflected to the distance image information which is input to the operation information learning model 91. The body cavity information included in the three-dimensional medical image is curved surface data indicating a shape (a shape of an inner wall of an organ) of an internal organ into which the endoscope 40 is inserted in a three-dimensional region including the imaging region of the virtual endoscopic image from which the distance image information is calculated. The curved surface data may be represented by, for example, a polynomial approximation expression or a set of points.

The intermediate layer has, for example, a single phase or a multilayer structure including one or a plurality of fully-connected layers, and each of a plurality of neurons included in the fully-connected layers outputs information indicating activation or deactivation based on the input distance image information and a value of the input body cavity information included in the three-dimensional medical image. The information processing apparatus 6 optimizes parameters used for arithmetic processing in the intermediate layer by using, for example, backpropagation or the like.

The output layer includes one or a plurality of neurons that output operation assistance information including the insertion direction of the endoscope 40, and outputs the operation assistance information based on the information indicating activation or deactivation of each neuron that is output from the intermediate layer. The operation assistance information including the insertion direction of the endoscope 40 may be displayed, for example, in a vector format in the coordinate system (internal body coordinate system) of the three-dimensional medical image, the vector format including a plurality of coordinate values and a plurality of rotation angles through which the distal end portion of the endoscope 40 sequentially passes in the insertion direction. Further, the operation assistance information may include a speed component with respect to a movement amount between values of adjacent coordinates through which the endoscope 40 sequentially passes.

Pieces of the inquiry data of the distance image information and the three-dimensional medical image (intermediate data) that are used as the training data and the operation assistance information including the insertion direction of the endoscope 40 and correlated with these pieces of the information are stored in a large amount as result data of examinations performed using the endoscope 40 in each medical institution. By using these pieces of the result data, a large amount of training data for learning the operation information learning model 91 can be generated.

Figure 6:
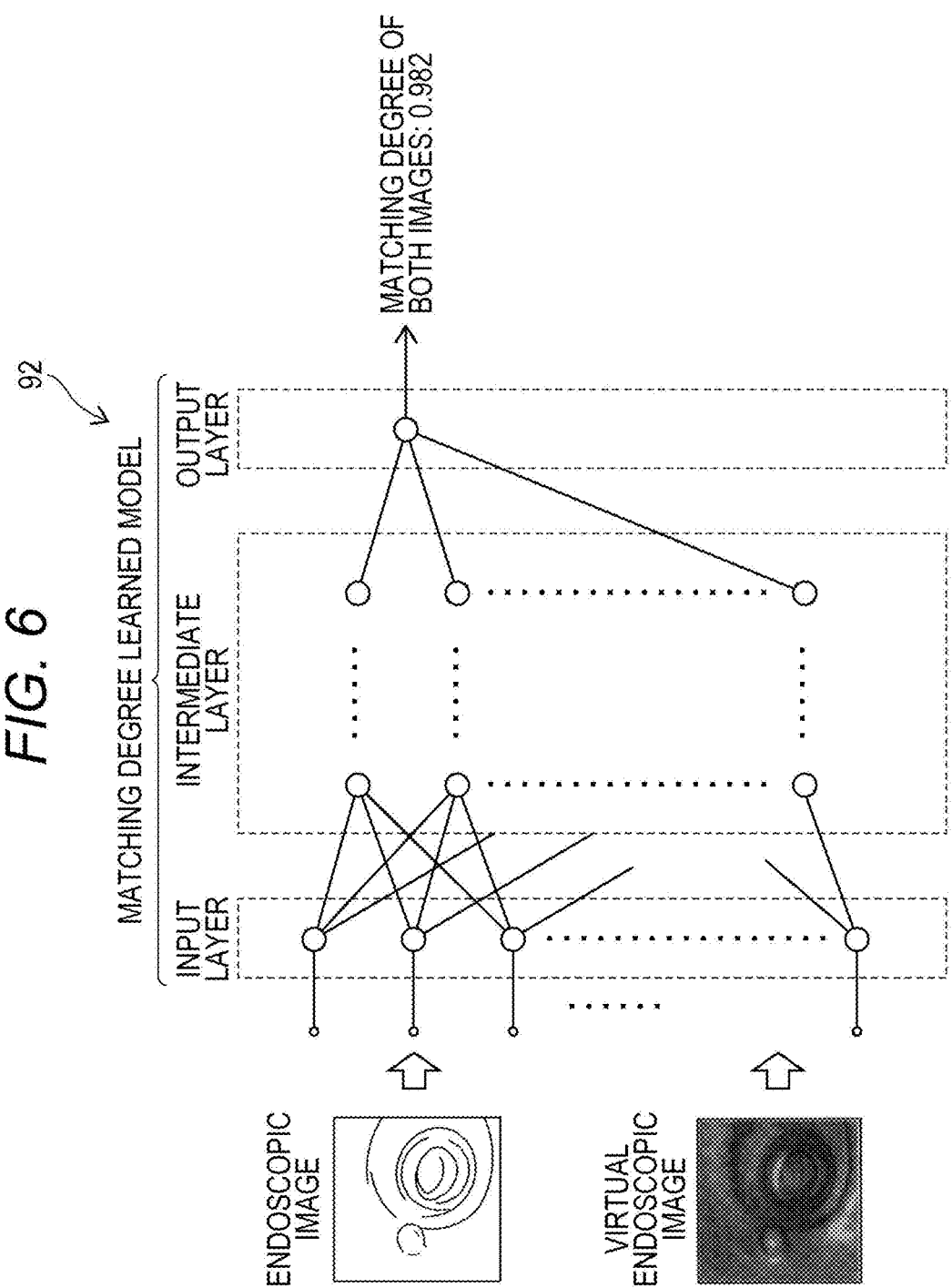
FIG. 6 is an explanatory diagram for explaining processing of outputting a matching degree with an endoscopic image using a matching degree learning model.

FIG. 6 is an explanatory diagram for explaining processing of outputting a matching degree with the endoscopic image using a matching degree learning model 92. The information processing apparatus 6 configures (generates) a neural network (matching degree learning model 92) that receives the endoscopic image and the virtual endoscopic image and outputs information such as a value indicating a matching degree of both images, by performing learning based on training data by setting, as inquiry data, the endoscopic image and the virtual endoscopic image and setting, as answer data, information on a matching degree of both images. It is assumed that, similarly to the operation information learning model 91, the matching degree learning model 92 learned using the training data is used as a program module which is a part of artificial intelligence software.

The input layer includes a plurality of neurons that receive pixel values of the endoscopic image and the virtual endoscopic image and transfer the input pixel values to an intermediate layer. The intermediate layer includes a plurality of neurons that extract image feature amounts of the endoscopic image and the virtual endoscopic image and transfer the extracted image feature amounts of both images to an output layer. The output layer includes one or a plurality of neurons that output information on a matching degree such as a value indicating the matching degree of the input endoscopic image and the input virtual endoscopic image, and outputs the information on the matching degree based on the image feature amounts of both images which are output from the intermediate layer.

For example, in a case where the matching degree learning model 92 is a convolutional neural network (CNN), the intermediate layer has a configuration in which a convolution layer that convolves a pixel value of each pixel which is input from the input layer and a pooling layer that maps (compresses) the pixel value convolved by the convolution layer are alternately connected, and the intermediate layer finally extracts the feature amounts of the endoscopic image and the virtual endoscopic image while compressing pixel information of the endoscopic image and pixel information of the virtual endoscopic image. The output layer includes, for example, a fully-connected layer and a soft max layer. The fully-connected layer calculates a cosine similarity according to an inner product of feature amount vectors based on image feature amounts of both images, and the soft max layer calculates a value (established value) indicating a matching degree based on the cosine similarity. Thus, the output layer outputs the value as information on the matching degree.

In configuration (generation) of the matching degree learning model 92, for example, by using a repository (learned model) such as DCNN implemented in a VGG16 model (caffemodel: VGG_ILSVRC_16_layers), transfer learning may be performed by training data based on the endoscopic image and the virtual endoscopic image, and the matching degree learning model 92 may be configured. The endoscopic image used as the training data and the virtual endoscopic image corresponding to the endoscopic image are stored in a large amount as result data of examinations performed using the endoscope 40 and the CT apparatus in each medical institution. By using these pieces of result data, a large amount of training data for learning the matching degree learning model 92 can be generated.

In the present embodiment, the operation information learning model 91 and the matching degree learning model 92 are described as a neural network (NN) such as a CNN. On the other hand, these learning models (91 and 92) are not limited to the N, and may be learning models (91 and 92) including another learning algorithm such as a support vector machine (SVM), a Bayesian network, or a regression tree.

Figure 7:
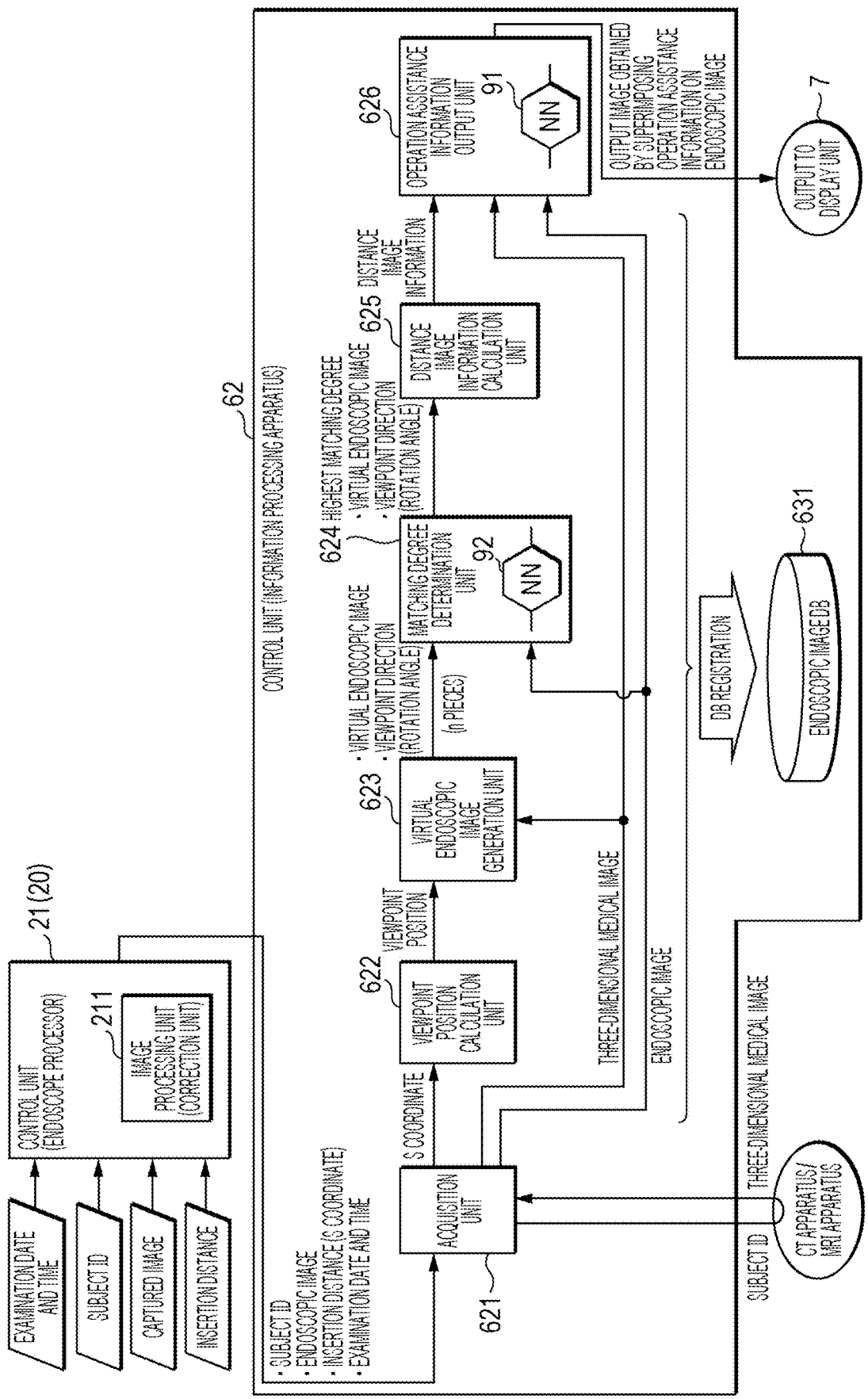
FIG. 7 is a functional block diagram exemplifying functional units included in a control unit of the information processing apparatus.

FIG. 7 is a functional block diagram exemplifying functional units included in the control unit of the information processing apparatus. The control unit 21 of the endoscope processor 20 (endoscope apparatus 10) executes the program stored in the main storage device 22, thereby functioning as the image processing unit 211. The control unit 62 of the information processing apparatus 6 functions as an acquisition unit 621, a viewpoint position calculation unit 622, a virtual endoscopic image generation unit 623, a matching degree determination unit 624, a distance image information calculation unit 625, and an operation assistance information output unit 626 by executing the program P stored in the storage unit 63.

The image processing unit 211 of the endoscope processor 20 performs various types of image processing such as gamma correction, white balance correction, and shading correction on the image (captured image) output from the endoscope, and outputs the image as the endoscopic image. The image processing unit 211 outputs (transmits) the generated endoscopic image and the examination date and time based on an imaging time of the endoscopic image to the information processing apparatus 6. The image processing unit 211 may further output the subject ID which is input from the keyboard 15 to the information processing apparatus 6. The image processing unit 211 may output, to the information processing apparatus 6, information on the insertion distance (S coordinate) of the endoscope 40 that is output from a sensor disposed in the insertion portion 44 (flexible tube) of the endoscope 40 in order to measure a surrounding environment of the endoscope 40. The image processing unit 211 may superimpose the information on the insertion distance of the endoscope 40 acquired from the sensor, for example, on the endoscopic image and display the superimposed image on the display device.

The sensor for acquiring the S coordinate which is the insertion distance of the endoscope 40 in the internal body is, for example, a temperature sensor, an optical sensor, a pressure sensor, a wet sensor (electrode), and a humidity sensor. For example, in a case where the sensor is an optical sensor, the optical sensor is disposed inside the insertion portion 44 (flexible tube). On the other hand, the optical sensor can receive light even in a case where the insertion portion 44 (flexible tube) is inserted into the body. Therefore, it is possible to determine that a portion where the optical sensor receives more light is outside the body and a portion where the optical sensor receives less light is inside the body. The control unit 21 of the endoscope processor 20 can calculate the S coordinate which is an insertion distance (length) of the insertion portion 44 (flexible tube) in the internal body by specifying the optical sensor at a boundary position corresponding to an insertion-allowance part in the body cavity based on a signal obtained by the optical sensor.

In a case of an upper endoscope, a roller encoder is attached to a mouthpiece or the like (not illustrated) in contact with the insertion portion 44 (flexible tube), and the roller encoder is rotated by a distance by which the insertion portion 44 (flexible tube) is inserted into the body. Thus, it is possible to acquire the S coordinate which is the insertion distance of the endoscope 40 in the internal body. The roller encoder attached to a mouthpiece or the like is rotated as the insertion portion 44 (flexible tube) moves forward and backward. Thus, the roller encoder can measure a length between the distal end portion 443 of the endoscope 40 inserted into the body and an opening communicating with a lumen such as a mouth or a nose, that is, an insertion distance of the insertion portion 44 (flexible tube). The roller encoder is electrically connected to the endoscope processor 20, and transmits the measured distance to the endoscope processor 20. Alternatively, an optical encoder or a magnetic encoder may he used instead of the roller encoder.

In addition, in a case of a lower endoscope, an object corresponding to a mouthpiece is attached to an anal portion, and an insertion distance of the endoscope can be measured. In a case where an auxiliary device for measuring the insertion distance of the endoscope 40 is attached to an insertion-allowance part in the body cavity that is an entrance of the subject, a passing distance of the endoscope 40 is measured. Thus, the S coordinate which is the insertion distance of the endoscope 40 in the internal body can be acquired. The auxiliary device may be, for example, a device that measures a distance using a scale of a magnetic field such as a linear scale attached to the insertion portion (flexible tube) 44 and a linear head attached to a mouthpiece, or may be a mouthpiece of the endoscope 40 to which a roller is attached. In a case where the endoscope 40 is inserted into a nose, an anus, or the like, an auxiliary device provided with a roller similar to the mouthpiece may be used. Further, a chip in which an insertion distance is recorded at regular intervals may be incorporated in the insertion portion (flexible tube) 44 of the endoscope 40. From S coordinate information that is recorded in the chip and is obtained by a mouthpiece or the like, the endoscope processor 20 can acquire the S coordinate which is the insertion distance of the endoscope 40 in the internal body.

The acquisition unit 621 acquires the subject ID, the examination date and time, the endoscopic image, and the S coordinate (insertion distance) output by the endoscope processor 20. Based on the acquired subject ID, the acquisition unit 621 acquires a three-dimensional medical image of the subject that is output from means configured to capture a three-dimensional image of the internal body, such as a CT apparatus, a cone beam CT apparatus, an MRI apparatus, or an ultrasonic diagnosis apparatus, which is communicatively connected. In a case where a three-dimensional medical image, which is output from another examination apparatus configured to capture a three-dimensional image of the internal body, such as a CT apparatus, a cone beam CT apparatus, an MRI apparatus, or an ultrasonic diagnosis apparatus, is already stored in, fir example, an external server (not illustrated), the information processing apparatus 6 may access the external server, and acquire the three-dimensional medical image of the subject based on the subject ID output from the endoscope processor 20.

The three-dimensional medical image is, for example, an image represented by volume data including tomographic image data, which is output from means configured to capture a three-dimensional image of the internal body, such as a CT apparatus, a cone beam CT apparatus, an MRI apparatus, or an ultrasonic diagnosis apparatus, or is an image represented by volume data which is output from a Multi Slice CT apparatus or an X-ray cone beam CT apparatus using an X-ray flat panel. In a case where an X-ray CT apparatus or a cone beam CT apparatus is used, for example, dual energy imaging may be performed by the X-ray CT, and an image in which a composition (body composition) of each pixel of a three-dimensional medical image can be identified by the effective mass number (effective-Z) may be used. In a case where an MRI apparatus is used, an image obtained by adding information on a composition (body composition) of each pixel of a three-dimensional medical image, such as fat or lactic acid, may be used.

Figure 8:
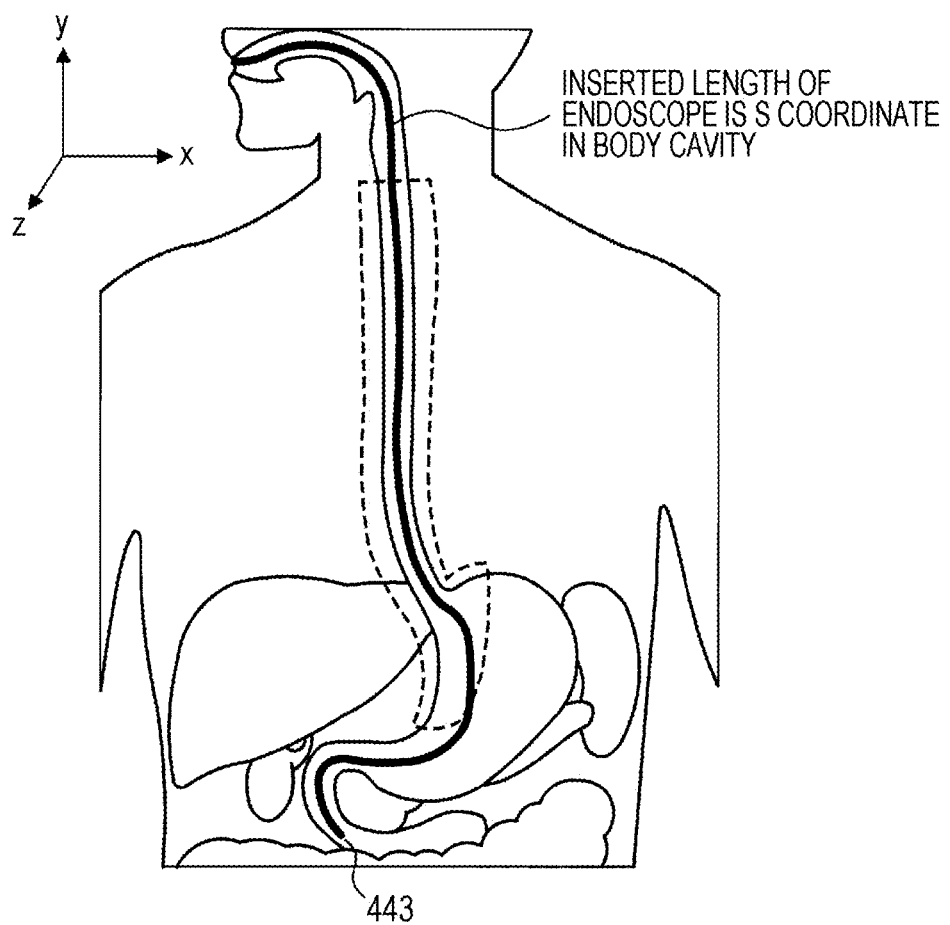
FIG. 8 is an explanatory diagram illustrating an insertion distance (a value of an S coordinate) of an endoscope.

The acquisition unit 621 outputs the acquired S coordinate to the viewpoint position calculation unit 622. Based on the acquired S coordinate, the viewpoint position calculation unit 622 calculates a coordinate (a coordinate in the internal body coordinate system) of the three-dimensional medical image corresponding to the S coordinate, that is, a viewpoint position at which the distal end portion 443 of the endoscope 40 is located. at the time when an image is captured by the endoscope 40. FIG. 8 is an explanatory diagram illustrating an insertion distance (a value of an S coordinate) of the endoscope 40. As illustrated in FIG. 8, in the three-dimensional medical image, a digestive organ captured by the endoscope 40 is represented by a three-dimensional shape. A space is formed inside an inner wall of the digestive organ, and the space serves as an insertion path through which the endoscope 40 is inserted. The S coordinate which is the insertion distance of the endoscope 40 corresponds to a place inside the insertion path (inside the inner wall of the digestive organ) and where a path length of the insertion path is substantially equal to the insertion distance. Thus, the coordinate of the distal end portion 443 of the endoscope 40 located inside the inner wall of the digestive organ can be calculated based on the S coordinate. The viewpoint position calculation unit 622 outputs information on the calculated viewpoint position to the virtual endoscopic image generation unit 623.

The acquisition unit 621 outputs the acquired three-dimensional medical image to the virtual endoscopic image generation unit 623. The virtual endoscopic image generation unit 623 generates a virtual endoscopic image based on the acquired three-dimensional medical image and the viewpoint position acquired from the viewpoint position calculation unit 622. The virtual endoscopic image is an image which is generated (reconfigured) based on the three-dimensional medical image obtained by capturing a tubular organ such as a trachea and a bronchus or an intestinal tract by X-ray CT, MRI, or X-ray cone beam CT and in which the inside of an organ (inside the body cavity) in the three-dimensional medical image is represented by a virtual endoscope. For example, CT imaging may be performed in a state where air is introduced into a large intestine, and a virtual endoscopic image of the large intestine may be generated (reconfigured) by performing volume rendering on a three-dimensional medical image obtained by the imaging from the inside of the large intestine.

The virtual endoscopic image generation unit 623 extracts voxel data of the organ in the subject from the acquired three-dimensional medical image. Examples of the organ include a large intestine, a small intestine, a kidney, a bronchus, a blood vessel, and the like. On the other hand, the organ is not limited thereto, and array be another organ. In the present embodiment, it is assumed that voxel data of the large intestine is extracted and acquired. For example, as a method of extracting a large intestine region, specifically, first, a plurality of axial images having a cross-section (axial cross-section) perpendicular to a body axis are reconfigured based on the three-dimensional medical image, for each axial image, a boundary between a body surface and the inside of the body is obtained by setting, as a threshold value, an X-ray CT value based on an X-ray absorption coefficient by a known method, and processing of separating an external body region and an internal body region is performed based on the body surface as a reference. For example, binarization processing using an X-ray CT value is performed on the reconfigured axial image, a contour is extracted by contour extraction processing, and the inside of the extracted contour is extracted as the internal body (human body) region. Next, binarization processing using a threshold value is performed on the axial image of the internal body region, and a candidate large-intestine region in each axial image is extracted. Specifically, since air is in a tube of the large intestine, a threshold value (for example, a value equal to or lower than −600 HU (Hounsfield Unit)) corresponding to a CT value of air is set, and binarization processing is performed. As a result, in each axial image, an air region in the internal body is extracted as a candidate large-intestine region. The virtual endoscopic image generation unit 623 reconfigures, as a virtual endoscopic image, an image obtained by central projection of projecting, on a predetermined projection plane, voxel data in a plurality of light beam directions radially extending around a viewpoint vector based on a rotation angle that is set as a viewpoint position and a viewpoint direction. As a specific method of the central projection, for example, a known volume rendering method or the like may be used.

For example, the virtual endoscopic image generation unit 623 sequentially generates a plurality of candidate virtual endoscopic images by changing a viewpoint direction, that is, a rotation angle ($\Theta x, \Theta y, \Theta z$) in a coordinate system of a three-dimensional medical image, for example, by a predetermined unit amount of 1°, from a viewpoint position corresponding to the coordinate of the distal end portion 443 of the endoscope 40 as a starting point. That is, for example, the virtual endoscopic image generation unit 623 may generate the plurality of virtual endoscopic images by projecting a three-dimensional shape of the inner wall of the digestive organ by a plurality of rotation angles which are set as the viewpoint direction, from the viewpoint position inside the digestive organ specified in the three-dimensional medical image. The virtual endoscopic image generation unit 623 associates the plurality of generated virtual endoscopic images with the viewpoint direction (rotation angle) used when the virtual endoscopic image is generated, and outputs the virtual endoscopic image to the matching degree determination unit 624.

The acquisition unit 621 outputs the acquired endoscopic image to the matching degree determination unit 624. Based on the acquired endoscopic image, the plurality of virtual endoscopic images acquired from the virtual endoscopic image generation unit 623, and the viewpoint direction (rotation angle) used when the virtual endoscopic image is generated, the matching degree determination unit 624 specifies the virtual endoscopic image having a highest matching degree with the acquired endoscopic image and the viewpoint direction (rotation angle) used when the virtual endoscopic image having a highest matching degree is generated. The matching degree determination unit 624 calculates a matching degree between the endoscopic image and the virtual endoscopic image by comparing the acquired endoscopic image with each of the plurality of virtual endoscopic images.

The matching degree determination unit 624 includes a matching degree learning model 92 that outputs information such as a value indicating a matching degree of both images based on the input endoscopic image and the input virtual endoscopic image. The matching degree determination unit 624 may input the acquired endoscopic image and the acquired virtual endoscopic image to the matching degree learning model 92, and output the virtual endoscopic image having a highest value among values (probability values) indicating the matching degrees output by the matching degree learning model 92, as the virtual endoscopic image corresponding to the endoscopic image.

Alternatively, the matching degree determination unit 624 is not limited to the case where the matching degree learning model 92 is included, and for example, may measure the matching degree by using an index indicating a correlation between a shade image of the endoscopic image and a shade image of the virtual endoscopic image. In order to quantitatively confirm the matching degree between the virtual endoscopic image and the endoscopic image, a level of the matching degree may be determined by confirming a correlation of shade image information obtained from luminance information. Alternatively, the matching degree determination unit 624 may compare a similarity between the plurality of configured virtual endoscopic images and the endoscopic image. The comparison of the similarity between the two images is performed by known image processing, and either pixel data level matching or matching of levels of features extracted from the images may be used. The virtual endoscopic image which is specified as having a highest matching degree with the endoscopic image by the matching degree determination unit 624 and the viewpoint direction (rotation angle) used to generate the virtual endoscopic image may be registered in the endoscopic image DB. The matching degree determination unit 624 outputs the virtual endoscopic image which is specified as having the highest matching degree with the endoscopic image and the viewpoint position and the viewpoint direction (rotation angle) used to generate the virtual endoscopic image, to the distance image information calculation unit 625.

In the present embodiment, the matching degree determination unit 624 specifies the virtual endoscopic image having a highest matching degree with the acquired endoscopic image. On the other hand, the present invention is not limited thereto. The matching degree determination unit 624 may specify the virtual endoscopic image of which the matching degree is equal to or higher than a predetermined value, as a virtual endoscopic image that is substantially identical to the acquired endoscopic image. By specifying the virtual endoscopic image of which the matching degree is equal to or higher than the predetermined value, it is not necessary to compare all the virtual endoscopic images generated as candidates. Thus, it is possible to reduce a calculation load and a processing time of the information processing apparatus 6. Alternatively, the matching degree determination unit 624 may specify a virtual endoscopic image having a smallest difference (difference index) from the acquired endoscopic image, as a virtual endoscopic image that is substantially identical to the acquired endoscopic image. The difference (difference index) between the endoscopic image and the virtual endoscopic image corresponds to a reciprocal of the matching degree between the endoscopic image and the virtual endoscopic image. Thus, by using an image comparison engine that calculates such a difference (difference index), it is possible to efficiently acquire a virtual endoscopic image that is substantially identical to the acquired endoscopic image.

In a case where the matching degree is not equal to or higher than the predetermined value, the matching degree determination unit 624 may regenerate a plurality of virtual endoscopic images again from a viewpoint position obtained by finely correcting the viewpoint position acquired from the viewpoint position calculation unit 622. calculate a matching degree between the plurality of regenerated virtual endoscopic images and the endoscopic image, and specify the virtual endoscopic image having a highest matching degree.

The distance image information calculation unit 625 calculates distance image information based on the virtual endoscopic image acquired from the matching degree determination unit 624. The distance image information is information on a distance between pixels in the virtual endoscopic image in the virtual endoscopic image. The distance between pixels means a distance in the coordinate system (internal body coordinate system) of the three-dimensional medical image, and is, for example, a distance in consideration of a depth in two internal body parts included in the virtual endoscopic image. The virtual endoscopic image is a two-dimensional image obtained by performing projection transformation on the three-dimensional medical image. A certain point in the virtual endoscopic image corresponds to a point in the three-dimensional medical image, and these points indicate the same position in the internal body part. A certain point in the virtual endoscopic image may be a pixel number (pixel coordinate) that is a smallest unit of an image, or may be, for example, a central portion of a local region (region including a plurality of pixels) that specifies a predetermined internal body part. By determining two certain points in this manner, a distance between the two points in the coordinate system of the three-dimensional medical image can be calculated. That is, the distance in the distance image information corresponds to a distance between two points in the coordinate system of the three-dimensional medical image corresponding to two points in the virtual endoscopic image.

The two points in the three-dimensional medical image are specified from the two points in the virtual endoscopic image. Based on coordinate values of the specified two points in the three-dimensional medical image, a distance and a vector between the two points can be calculated. By reflecting the calculated distance and the calculated vector between the two points in the three-dimensional medical image to the virtual endoscopic image, as a distance and a vector between two points in the virtual endoscopic image corresponding to the two points, it is possible to generate a distance image, that is, a virtual endoscopic image (distance image) obtained by reflecting the distance information in the coordinate system of the three-dimensional medical image to the virtual endoscopic image. The distance image information calculation unit 625 may output the virtual endoscopic image (distance image) to which the information on the distance between pixels is reflected as the distance image information. Further, the distance image information calculation unit 625 may output the virtual endoscopic image to which the viewpoint position and the direction of the endoscope 40 used to generate the virtual endoscopic image are reflected.

The endoscopic image corresponds to a virtual endoscopic image reconfigured (generated) from the three-dimensional medical image based on the position (viewpoint position) and the imaging direction (viewpoint direction) of the endoscope 40 that captures the endoscopic image. Thus, the distance image information based on the virtual endoscopic image corresponding to the endoscopic image can also be applied to the endoscopic image. That is, a distance between two points in the endoscopic image corresponds to a distance (a distance in the distance image, a distance in the coordinate system of the three-dimensional medical image) between two points in the virtual endoscopic image corresponding to the endoscopic image. Therefore, by applying the distance image information included in the distance image (virtual endoscopic image) to the endoscopic image, it is possible to determine the distance information (distance image information in the endoscopic image) such as a distance between internal body parts included in the endoscopic image and a size of the internal body part.

The operation assistance information output unit 626 acquires the distance image information which is output from the distance image information calculation unit 625 and the viewpoint position and the direction (rotation angle) of the endoscope 40. The operation assistance information output unit 626 acquires the three-dimensional medical image output from the acquisition unit 621, and extracts body cavity information included in the three-dimensional medical image. As described above, the body cavity information included in the three-dimensional medical image is, for example, curved surface data indicating a shape (a shape of an inner wall of an organ) of an internal organ into which the endoscope 40 is inserted in a three-dimensional region including the imaging region of the virtual endoscopic image from which the distance image information is calculated.

The operation assistance information output unit 626 includes an operation information learning model 91 that outputs operation assistance information including an entry direction of the endoscope 40 based on the input distance image information, the viewpoint position and the direction of the endoscope 40, and the body cavity information which is included in the three-dimensional medical image and is represented by curved surface data. The operation assistance information output unit 626 inputs, to the operation information learning model 91, the acquired distance image information, the viewpoint position and the direction of the endoscope 40, and the body cavity information which is included in the three-dimensional medical image and is represented by curved surface data, and acquires the operation assistance information which includes the entry direction of the endoscope 40 and is output from the operation information learning model 91.

As described above, the operation assistance information which is output from the operation information learning model 91 includes, for example, information on an insertion direction, an insertion amount, or an insertion speed of the endoscope 40, from the viewpoint position and the direction of the endoscope 40 at the present time, that is, at the time of capturing the endoscopic image, to a target point indicating an insertion destination. The operation assistance information may be displayed in a vector format or a matrix format in the coordinate system (internal body coordinate system) of the three-dimensional medical image, the format including a plurality of coordinate values and a plurality of rotation angles through which the distal end portion 443 of the endoscope 40 sequentially passes from the viewpoint position of the endoscope 40 to the target point. By using the plurality of coordinate values and the plurality of rotation angles through which the endoscope 40 sequentially passes, it is possible to determine an insertion path of the endoscope 40 by connecting the plurality of coordinate values as path points. When calculating each of the coordinate values as the path points, the operation assistance information output unit 626 may perform correction according to hardness of the insertion portion (flexible tube) 44 and calculate the coordinate values.

The operation assistance information output unit 626 acquires the endoscopic image output from the acquisition unit 621, generates, for example, image data obtained by superimposing the operation assistance information on the endoscopic image, and outputs the image data to the display unit 7. The display unit 7 displays the endoscopic image obtained by superimposing the operation assistance information on the endoscopic image, based on the image data acquired from the operation assistance information output unit 626.

The subject ID, the examination date and time, the endoscopic image, the S coordinate, and the three-dimensional medical image, which are acquired by the acquisition unit 621, the virtual endoscopic image calculated by the matching degree determination unit 624, and the information on the viewpoint position and the direction of the endoscope 40 are stored in the endoscopic image DB in association with each other. That is, the control unit of the information processing apparatus may function as a DB registration unit, and register and store various images, information, or data acquired or calculated by the acquisition unit 621 and the matching degree determination unit 624 in the endoscopic image DB.

Figure 9:
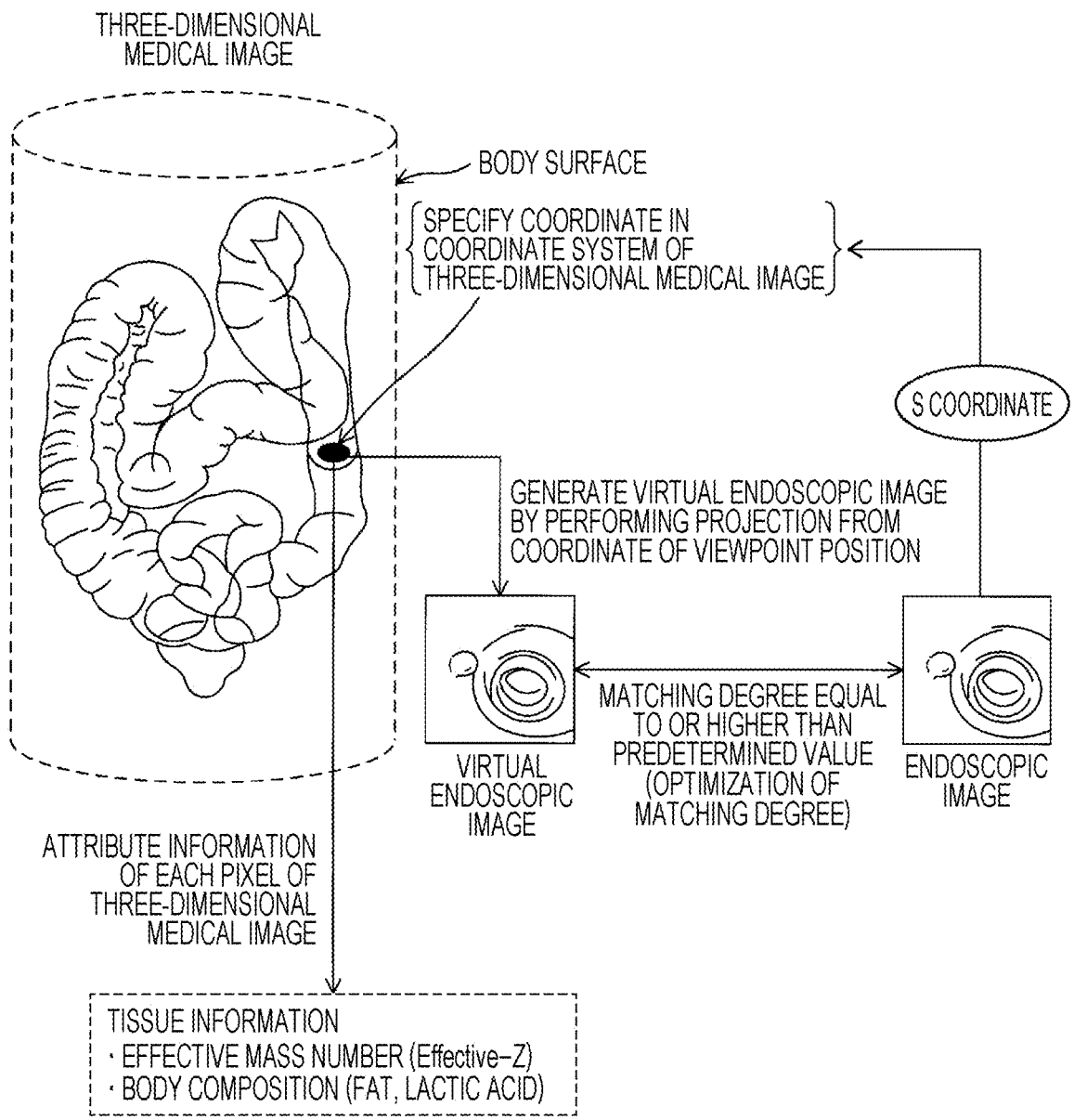
FIG. 9 is an explanatory diagram on a relationship between an endoscopic image and a three-dimensional medical image.

FIG. 9 is an explanatory diagram on a relationship between the endoscopic image and the three-dimensional medical image. In FIG. 9, a relationship between the three-dimensional medical image, the virtual endoscopic image, and the endoscopic image is represented in an object-oriented manner.

As described above, the three-dimensional medical image, the virtual endoscopic image, and the endoscopic image which are registered in the endoscopic image DB 631 are associated with each other based on the viewpoint position and the viewpoint direction at the time of capturing the endoscopic image. The viewpoint position corresponds to a coordinate (x, y, z) in the coordinate system (internal body coordinate system) of the three-dimensional medical image. The viewpoint direction corresponds to a rotation angle (Θx, Θy, Θz) in an x-axis, a y-axis, and a z-axis in the coordinate system (internal body coordinate system) of the three-dimensional medical image.

Each pixel of the endoscopic image corresponds to each pixel of the virtual endoscopic image (the virtual endoscopic image having a highest matching degree with the endoscopic image). The virtual endoscopic image is an image generated by setting, as a starting point, the viewpoint position based on the three-dimensional medical image, and performing projection by vector conversion using a viewpoint vector defined by the viewpoint direction (rotation angle). A coordinate in the coordinate system (internal body coordinate system) of the three-dimensional medical image is determined by a pixel of the virtual endoscopic image.

As described above, since each of the pixels of the virtual endoscopic image corresponds to each of the pixels of the endoscopic image, it is possible to determine the coordinate of the pixel of the endoscopic image, that is, the coordinate of the internal body part included in the endoscopic image in the coordinate system (internal body coordinate system) of the three-dimensional medical image, based on the pixel of the virtual endoscopic image. That is, by using the virtual endoscopic image as an intermediate medium, it is possible to associate the pixel (internal body part) of the endoscopic image with the coordinate in the coordinate system (internal body coordinate system) of the three-dimensional medical image.

Color information and narrow band pixel information of pixels of the endoscopic image may be added to the three-dimensional medical image, and the three-dimensional medical image may be registered in the endoscopic image DB 631. In a case where the pixel information of the endoscopic image, such as the difference and the color information, is added to the three-dimensional medical image, it is desirable to perform luminance correction by using an imaging light source 446. As described above, the distance between the pixel of the endoscopic image and the viewpoint position (a position of the imaging light source 446) is calculated on the coordinate system of the three-dimensional medical image. Therefore, brightness included in the pixel information of the endoscopic image may be corrected based on a reciprocal obtained by squaring the calculated distance. In a case where there are a plurality of endoscopic images including pixels located at the same coordinates in the coordinate system of the three-dimensional medical image, the pixel information may be added to the three-dimensional medical image by applying a weight according to the distance, such as giving preference to the endoscopic image having a shortest distance, and performing load averaging or simple averaging.

In imaging of a three-dimensional medical image, in a case where an X-ray CT apparatus or a cone beam CT apparatus is used, for example, dual energy imaging may be performed, and an image in which a composition (body composition) of each pixel of a three-dimensional medical image can be identified by the effective mass number (effective-Z) may be used. Further, in a case where an MRI apparatus is used, an image obtained by adding information on a composition (body composition) of each pixel of a three-dimensional medical image, such as fat or lactic acid, may be used. As described above, by adding information on the body composition, such as the effective mass number (effective-Z), fat, or lactic acid, to the composition of each pixel of the three-dimensional medical image, it is possible to provide, for a doctor or the like, information in which the added information and the endoscopic image associated with the coordinate specified by each pixel of the three-dimensional medical image are associated with each other.

Figure 10:
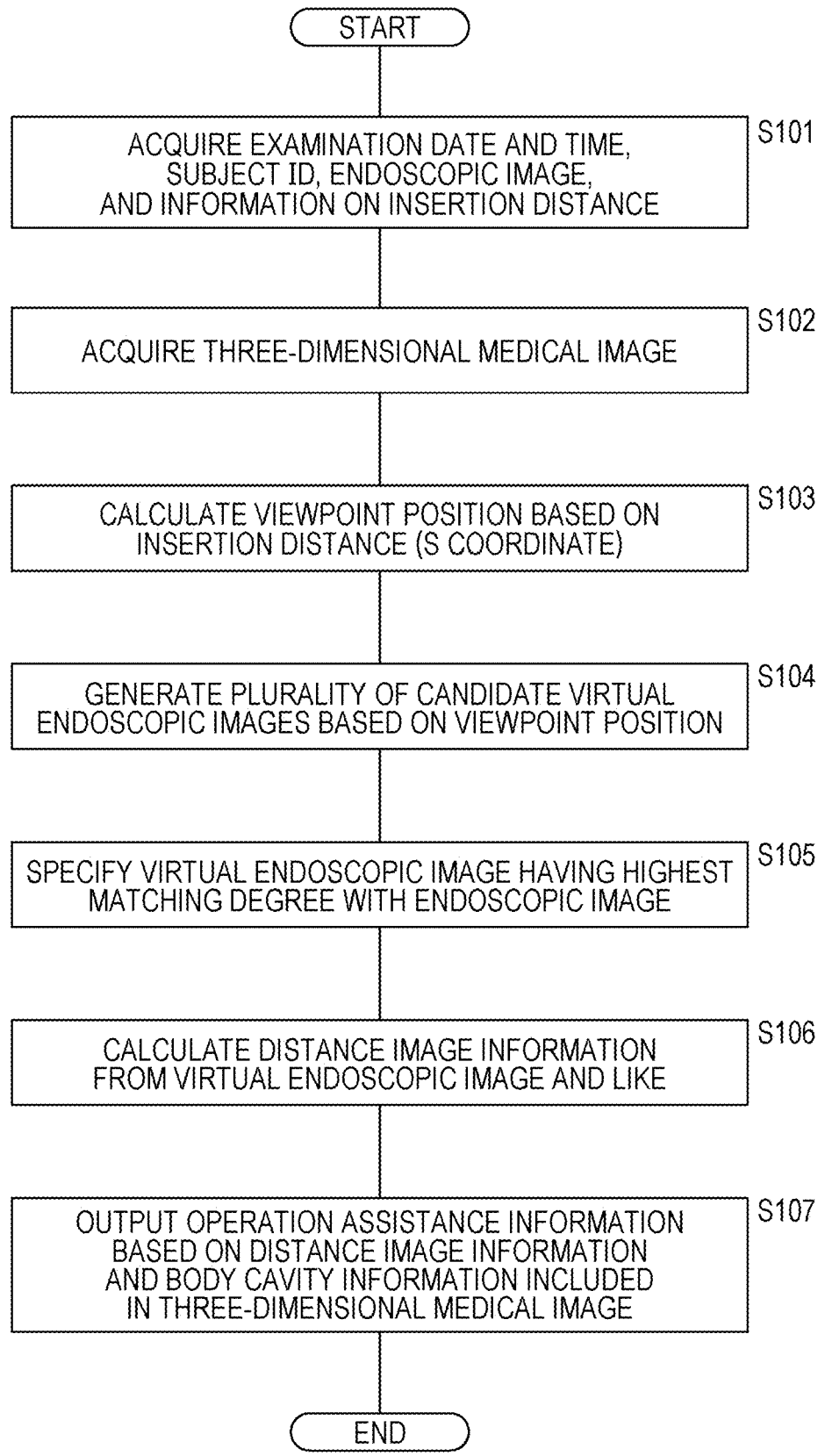
FIG. 10 is a flowchart illustrating an example of a processing procedure performed by the control unit of the information processing apparatus.

FIG. 10 is a flowchart illustrating an example of a processing procedure performed by the control unit 62 of the information processing apparatus 6. For example, the information processing apparatus 6 starts processing of the flowchart based on contents input from the input unit 8 connected to the information processing apparatus 6.

The control unit 62 of the information processing apparatus 6 acquires the examination date and time, the subject ID, the endoscopic image, and the information on the insertion distance which are output from the endoscope processor 20 (step S101). The endoscopic image acquired by the control unit 62 from the endoscope processor 20 may be a still image or a moving image. In addition to acquisition of the endoscopic image, the control unit 62 acquires information on the insertion distance of the endoscope 40 which is output from the optical sensor or the like, the examination dale and time (imaging date and time of the endoscopic image), and attribute information of the subject such as the subject ID.

The control unit 62 of the information processing apparatus 6 acquires a three-dimensional medical image which is output from an examination apparatus configured to capture a three-dimensional image of the internal body, such as a CT apparatus, an MRI apparatus, or an ultrasonic diagnosis apparatus (step S102). The three-dimensional medical image may be acquired by the information processing apparatus 6 communicatively connected to an examination apparatus configured to capture a three-dimensional image of the internal body, such as a CT apparatus, an MRI apparatus, or an ultrasonic diagnosis apparatus. Alternatively, in a case where a three-dimensional medical image, which is output front an examination apparatus configured to capture a three-dimensional image of the internal body, such as a CT apparatus, an MRI apparatus, or an ultrasonic diagnosis apparatus, is already stored in, for example, an external server (not illustrated), the information processing apparatus 6 may access the external server, and acquire the three-dimensional medical image of the subject based on the subject ID output from the endoscope processor 20. Alternatively, in a case where the endoscope processor 20 is communicatively connected to an examination apparatus configured to capture a three-dimensional image of the internal body, such as a CT apparatus, an MRI apparatus, or an ultrasonic diagnosis apparatus, the control unit 62 of the information processing apparatus 6 may acquire a three-dimensional medical image from the examination apparatus configured to capture a three-dimensional image of the internal body, such as a CT apparatus, an MRI apparatus, or an ultrasonic diagnosis apparatus, via the endoscope processor 20.

The control unit 62 of the information processing apparatus 6 calculates the viewpoint position based on the insertion distance (S coordinate) (step S103). The control unit 62 acquires information on the insertion distance (S coordinate) from, for example, an optical sensor or the like disposed inside the insertion portion 44 (flexible tube) of the endoscope 40 via the endoscope processor 20, and calculates a coordinate of the distal end portion 443 of the endoscope 40 located inside the inner wall of the digestive organ into which the endoscope 40 is inserted based on the acquired insertion distance (S coordinate) and the three-dimensional medical image. The coordinate is a coordinate in the coordinate system (internal body coordinate system) of the three-dimensional medical image when a predetermined point is set as an origin.

The control unit 62 of the information processing apparatus 6 generates a plurality of candidate virtual endoscopic images based on the viewpoint position (step S104). The control unit 62 sequentially generates a plurality of candidate virtual endoscopic images by changing the viewpoint direction, that is, the rotation angle ($\Theta x$, $\Theta y$, $\Theta z$) in the coordinate system of the three-dimensional medical image by a predetermined unit amount, from the viewpoint position corresponding to the coordinate of the distal end portion 443 of the endoscope 40 as a starting point. For example, in a case where the predetermined unit amount is 10°, the control unit 62 has 36 resolutions for the rotation angle of each axis. That is, the control unit 62 may generate 46656 (36 to the power of 3) candidate virtual endoscopic images.

The control unit 62 of the information processing apparatus 6 specifies a virtual endoscopic image having a highest matching degree with the endoscopic image among the plurality of generated virtual endoscopic images (step S105). The control unit 62 specifies a virtual endoscopic image having a highest matching degree with the endoscopic image, for example, by using the matching degree learning model 92. Alternatively, the control unit 62 may measure the matching degree by using an index indicating a correlation between a shade image of the endoscopic image and a shade image of the virtual endoscopic image. The control unit 62 specifies a virtual endoscopic image having a highest matching degree and the viewpoint position and the direction (rotation angle) at the time of generating the virtual endoscopic image.

The control unit 62 of the information processing apparatus 6 calculates distance image information from the acquired virtual endoscopic image (step S106). The control unit 62 calculates distance image information that is information on the distance between pixels in the virtual endoscopic image.

The control unit 62 of the information processing apparatus 6 outputs operation assistance information based on the distance image information and the body cavity information included in the three-dimensional medical image (step S107). The control unit 62 extracts, the body cavity information included in the acquired three-dimensional medical image, as curved surface data indicating a shape (a shape of an inner wall of an organ) of an internal organ into which the endoscope 40 is inserted in a three-dimensional region including the imaging region of the virtual endoscopic image from which the distance image information is calculated. The control unit 62 inputs, to the operation information learning model 91, the extracted curved surface data, the distance image information, and information indicating the position and the direction of the endoscope 40, and outputs the operation assistance information output by the operation information learning model 91.

When outputting the operation assistance information, the control unit 62 may generate image data obtained by superimposing the operation assistance information on the endoscopic image, the virtual endoscopic image, or the three-dimensional medical image, and output the image data to, for example, the display unit. The display unit displays the endoscopic image, the virtual endoscopic image, or the three-dimensional medical image on which the operation assistance information is superimposed, based on the image data output from the control unit 62 of the information processing apparatus 6.

The operation assistance information superimposed on the endoscopic image, the virtual endoscopic image, or the three-dimensional medical image includes the insertion direction, the insertion amount, and the insertion speed of the endoscope 40, and information on the target point coordinate indicating the insertion destination. Thus, useful information can be provided for an operator of the endoscope 40 such as a doctor, and it is possible to contribute to diagnosis assistance for a doctor and the like.

Figure 11:
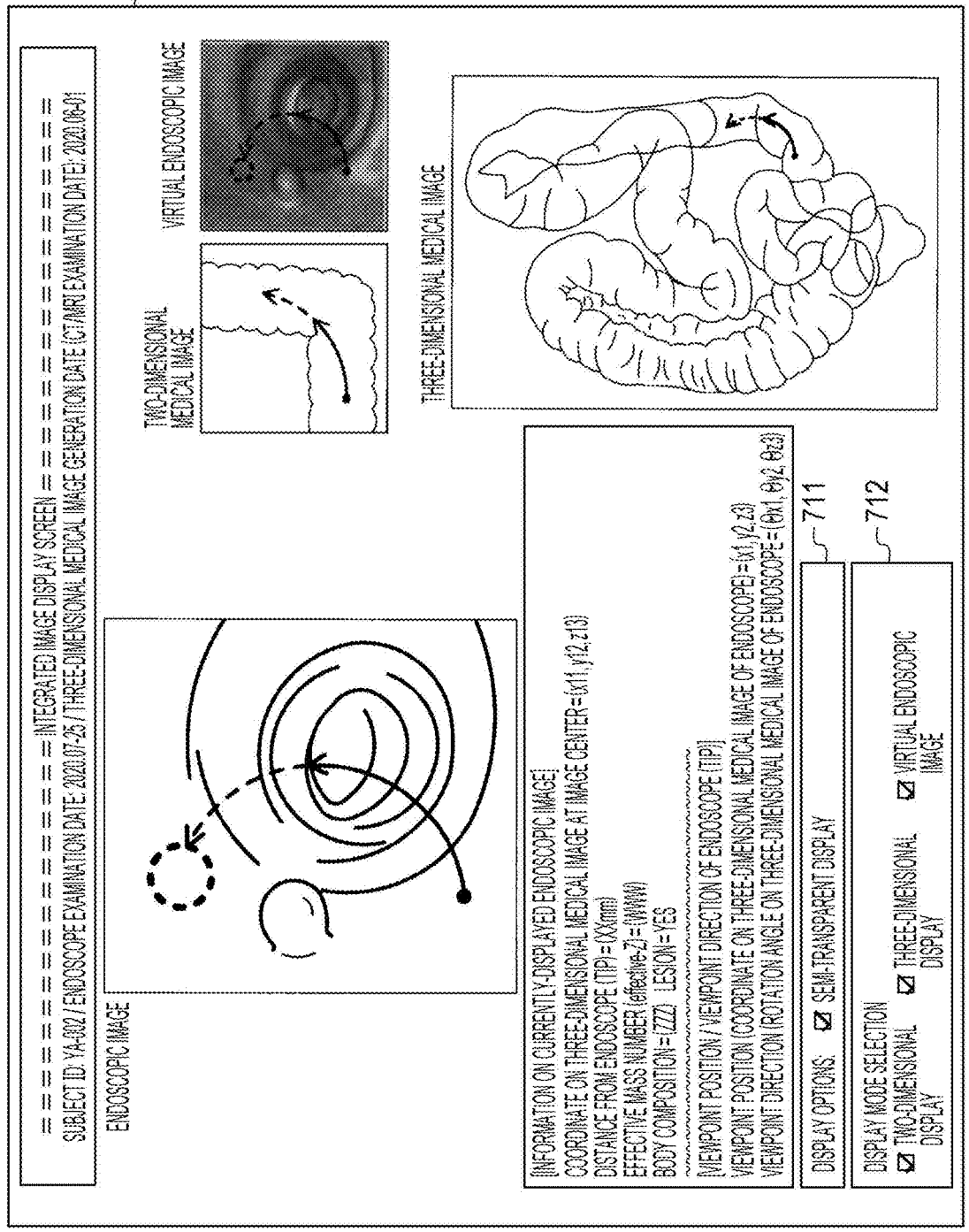
FIG. 11 is an explanatory diagram illustrating an aspect of an integrated image display screen.

FIG. 11 is an explanatory diagram illustrating an aspect of an integrated image display screen 71. As described above, the control unit 62 of the information processing apparatus 6 generates image data including the endoscopic image, the virtual endoscopic image, or the three-dimensional medical image on which the operation assistance information such as the insertion direction of the endoscope 40 is superimposed, and outputs the image data to the display unit 7. The integrated image display screen 71 is an example of a display screen configured by the image data, and the display unit 7 displays the integrated image display screen 71 based on the image data.

The integrated image display screen 71 includes, for example, a region for displaying bibliographic mailers such as a subject ID, a region for displaying an endoscopic image, a region for displaying a three-dimensional medical image, a region for displaying a two-dimensional medical image, a region for displaying a virtual endoscopic image, and a region for displaying information on the currently-displayed endoscopic image, a viewpoint position from which the endoscopic image is captured, and the like.

In the region for displaying bibliographic matters such as a subject ID, bibliographic matters in data management, such as the subject ID used to specify the three-dimensional medical image corresponding to the endoscopic image, the examination date and time by the endoscope 40, and a generation date of the three-dimensional medical image, are displayed.

In the region for displaying the endoscopic image, the endoscopic image currently captured by the endoscope 40 is displayed in real time. The operation assistance information such as the insertion direction of the endoscope 40 is displayed by being superimposed on the endoscopic image. In accordance with setting of a display option to be described later, the endoscopic image may be displayed in a translucent manner, and the internal body part located on an inner side of the internal wall surface displayed in the endoscopic image may be displayed by a dotted line, the internal body part being extracted from the virtual endoscopic image corresponding to the endoscopic image. The internal body part displayed by a dotted line in translucent display may be, for example, a part of a lesion candidate extracted based on shape information of the internal body part specified in the three-dimensional medical image.

In the region for displaying the three-dimensional medical image, the internal body part such as a digestive organ represented in the three-dimensional medical image is displayed as a three-dimensional object, and the operation assistance information such as the viewpoint position of the endoscope 40 and the insertion direction of the endoscope 40 when the viewpoint position is set as a starting point is displayed by being superimposed. By dragging a part of the three-dimensional object, the three-dimensional object can be rotated. In the three-dimensional medical image, a position of a part of a lesion candidate extracted based on shape information of an internal body part specified in the three-dimensional medical image may he displayed, for example, in a highlighted state.

In the region for displaying the two-dimensional medical image, a two-dimensional medical image obtained by projecting, on the three-dimensional medical image, a region where the operation assistance information such as the insertion direction of the endoscope 40 is superimposed is displayed. A projection vector used for generating the two-dimensional medical image may be determined in accordance with a rotation state of the three-dimensional object displayed in the region where the three-dimensional medical image is displayed.

In the region for displaying the virtual endoscopic image, a virtual endoscopic image having a highest matching degree with the endoscopic image is displayed, the endoscopic image being displayed in the region for displaying the endoscopic image. The operation assistance information such as the insertion direction of the endoscope 40 may be displayed by being superimposed on the virtual endoscopic image as in the endoscopic image.

In the region for displaying the viewpoint position when the endoscopic image is captured, the position (viewpoint position) and the viewpoint direction (rotation angle) of the endoscope 40 in the body at the time of capturing the endoscopic image are displayed, the endoscopic image being displayed in the region for displaying the endoscopic image. As described above, the control unit 62 (acquisition unit 621) of the information processing apparatus 6 continuously acquires the endoscopic image and the S coordinate indicating the insertion distance of the endoscope 40 from the processor for the endoscope 40, and continuously calculates the position (viewpoint position) of the distal end portion of the endoscope 40 based on the acquired S coordinate. Further, the control unit 62 (acquisition unit 621) of the information processing apparatus 6 continuously calculates the direction (rotation angle) of the distal end portion of the endoscope 40 when specifying the virtual endoscopic image corresponding to the endoscopic image based on the matching degree with the endoscopic image. Therefore, in the region for displaying the viewpoint position when the endoscopic image is captured, the viewpoint position and the viewpoint direction of the endoscope 40 are displayed in real time according to an operation of the endoscope 40 by a doctor or the like.

In the region for displaying information of the currently-displayed endoscopic image, for example, information on an internal body part or a pixel at the image center of the currently-displayed endoscopic image is displayed. As described above, in the three-dimensional medical image, the information on the internal body part (pixel) includes information on the composition (body composition) of each pixel of the three-dimensional medical image, such as the effective mass number (effective-Z), fat, or lactic acid which is substance determination information based on X-rays. Therefore, it is possible to display the information on the body composition such as the effective mass number (effective-Z) extracted from the three-dimensional medical image, in the region, based on the coordinate in the internal body coordinate system indicating the image center of the endoscopic image. Further, the presence or absence of a lesion in an internal body part included in the currently-displayed endoscopic image can also be displayed in the region by using a learning model that receives the endoscopic image and outputs information on the presence or absence of a lesion. As the learning model that outputs the information on the presence or absence of a lesion based on the input endoscopic image, for example, any object detection algorithm having a function of a segmentation network such as CNN, regions with convolutional neural network (RCNN), Fast RCNN, Faster-RCNN, single shot multibox detector (SSD), or You Only Look Once (YOLO) may be used.

As described above, since the viewpoint position of the endoscope 40 is continuously calculated according to the operation of the endoscope 40 by a doctor or the like, for example, the information on the distance between the viewpoint position and the image center of the currently-displayed endoscopic image may be calculated, and the calculated distance (distance from the viewpoint position to the pixel at the image center) may be displayed in the region.

The integrated image display screen 71 includes an input region for receiving an input on a display mode, and in the input region, for example, a display option field 711 for setting a display option and a display mode selection field 712 for receiving selection of a plurality of display modes are disposed.

The display option field 711 is provided with a toggle switch for setting whether to translucently display the endoscopic image, the virtual endoscopic image, or both images. In a case where a check is input in the toggle switch, based on shape data of the internal body part included in the virtual endoscopic image or the three-dimensional medical image, processing of making the internal wall surface displayed in the endoscopic image translucent is performed, and the internal body part located on an inner side of the internal wall surface is displayed by a dotted line. As described above, the internal body part located on an inner side of the internal wall surface may be, for example, a part of a lesion candidate extracted based on shape information of the internal body part specified in the three-dimensional medical image.

The display mode selection field 712 is provided with toggle switches for selecting the virtual endoscopic image, the two-dimensional medical image, and the three-dimensional medical image which are to be displayed together with the endoscopic image. In a case where a check is input in the toggle switch corresponding to any one of these images, the image corresponding to the check is displayed. According to the check which is input in each of the toggle switches in the display mode selection field 712, it is possible to select a case of displaying any one or two images of the virtual endoscopic image, the two-dimensional medical image, and the three-dimensional medical image and a case of displaying all of these three images. A display size of the image may be resized according to the number of images to be displayed.

According to the present embodiment, based on the endoscopic image, a three-dimensional medical image is acquired by imaging an internal body portion of the subject by, for example, an examination apparatus configured to capture a three-dimensional image of an internal body portion of the subject, such as X-ray CT, X-ray cone beam CT, MRI-CT, or an ultrasonic diagnosis apparatus, the virtual endoscopic image is reconfigured from the acquired three-dimensional medical image, and distance image information in the endoscopic image is calculated based on the virtual endoscopic image and the endoscopic image. Therefore, by using, in addition to the endoscopic image, the virtual endoscopic image configured with the three-dimensional medical image including coordinate information in a three-dimensional space, it is possible to accurately calculate distance image information in the endoscopic image. Based on the calculated distance image information and the three-dimensional medical image or the virtual endoscopic image, it is possible to efficiently output the operation assistance information on the operation of the endoscope. The X-ray CT, the X-ray cone beam CT, the MRI-CT, or the ultrasonic diagnosis apparatus is an example of an examination apparatus configured to capture a three-dimensional image of an internal portion of a body, and is not limited thereto. The three-dimensional medical image is not limited to a case of being acquired from any of these examination apparatuses, and may be acquired from a plurality of examination apparatuses.

According to the present embodiment, the operation assistance information includes the information on the insertion direction or the insertion speed of the endoscope 40. Thus, by outputting the operation assistance information, for an operator of the endoscope 40 such as a doctor, it is possible to efficiently perform diagnosis assistance on an operation of the endoscope 40.

According to the present embodiment, the operation assistance information is displayed, for example, on the integrated image display screen 71 by being superimposed on the currently-captured endoscopic image, and the three-dimensional medical image, the two-dimensional medical image, or the virtual endoscopic image, which corresponds to the endoscopic image. Therefore, visibility of the operation assistance information for an operator of the endoscope 40 such as a doctor can be improved, and thus it is possible to efficiently perform diagnosis assistance for a doctor or the like.

Second Embodiment

Figure 12:
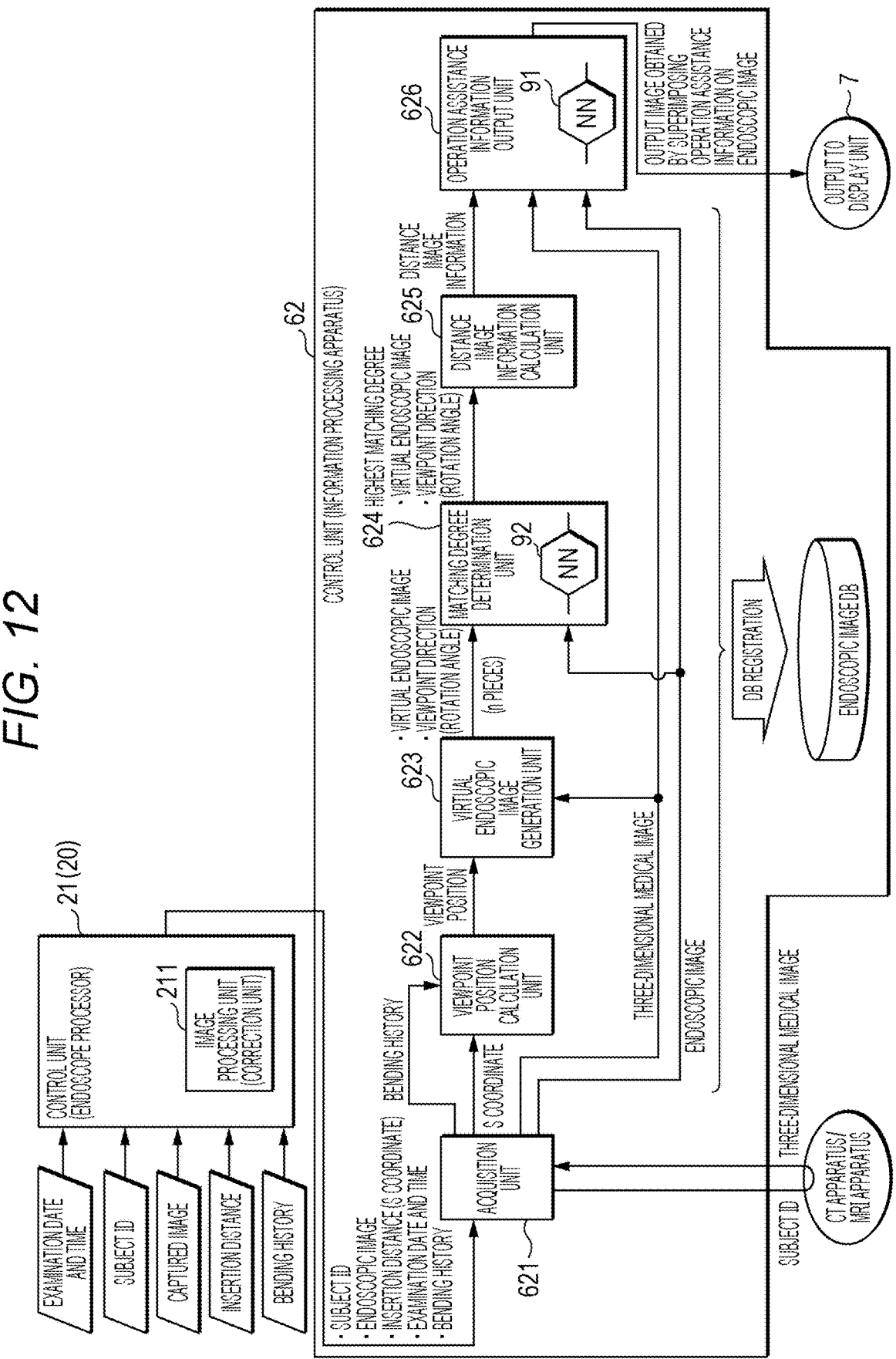
FIG. 12 is a functional block diagram exemplifying functional units included in a control unit of an information processing apparatus according to a second embodiment (bending history).

The information processing apparatus 6 according to a second embodiment is different from the information processing apparatus according to the first embodiment in that the viewpoint position is corrected based on a bending history acquired from the endoscope processor 20. FIG. 12 is a functional block diagram exemplifying functional units included in the control unit of the information processing apparatus according to a second embodiment (bending history).

The control unit 21 of the endoscope processor 20 acquires bending history information of the endoscope 40 inserted into the body, and determines an insertion situation of the endoscope 40 according to the acquired bending history information. The control unit 21 of the endoscope processor 20 ma detect the bending history information by using, for example, an endoscope-insertion-shape detection device (not illustrated) connected to the endoscope processor 20. For example, as disclosed in JP 2019-37643 A, the endoscope-insertion-shape detection device may be a device in which a plurality of magnetic coils are disposed inside the insertion portion 44 of the endoscope 40 at predetermined intervals along a longitudinal direction of the insertion portion 44. The bending history information indicates a physical parameter or information on bending such as a bending angle or a bending direction.

As in the first embodiment, the acquisition unit 621 of the information processing apparatus 6 acquires an endoscopic image from the endoscope processor 20, and further acquires bending history information. The acquisition unit 621 outputs the acquired bending history information to the viewpoint position calculation unit 622.

The viewpoint position calculation unit 622 corrects the insertion distance (S coordinate) based on the acquired bending history information, and calculates the viewpoint position based on the corrected insertion distance (S coordinate) as in the first embodiment. The viewpoint position calculation unit 622 detects a shape (for example, rightward bending by 30 degrees) of the insertion portion 44 by arithmetic processing according to the bending angle and the bending direction. The control unit 21 recalculates (corrects) the S coordinate that is the insertion distance based on the detected shape of the insertion portion 44. Thereafter, each functional unit such as the virtual endoscopic image generation unit 623 performs processing as in the first embodiment, and the operation assistance information output unit 626 generates and outputs operation assistance information as in the first embodiment.

The viewpoint position calculation unit 622 of the information processing apparatus 6 corrects the viewpoint position based on the bending history acquired from the endoscope processor 20, and the present invention is not limited thereto. The control unit 21 of the endoscope processor 20 may correct the insertion distance based on the acquired bending history information, and output the corrected insertion distance to the information processing apparatus 6. The acquisition unit 621 of the information processing apparatus 6 may acquire the viewpoint position which is corrected based on the bending history information by the control unit 21 of the endoscope processor 20, and the subsequent processing may be performed as in the first embodiment.

The position information for associating the endoscopic image with the three-dimensional medical image is calculated based on the information on the bending history, the information on the insertion distance, and the length of the insertion path of the endoscope 40 that is specified in the three-dimensional medical image. By correcting the information on the insertion distance based on the information on the bending history, accuracy of the insertion distance (S coordinate) can be improved. Therefore, it is possible to accurately specify the viewpoint position (coordinate) and the viewpoint direction (rotation angle) of the endoscope 40 in the coordinate system of the three-dimensional medical image at the time of capturing the endoscopic image. Thus, it is possible to efficiently generate a suitable virtual endoscopic image. Thereby, it is possible to further improve accuracy in association between the endoscopic image and the three-dimensional medical image.

Figure 13:
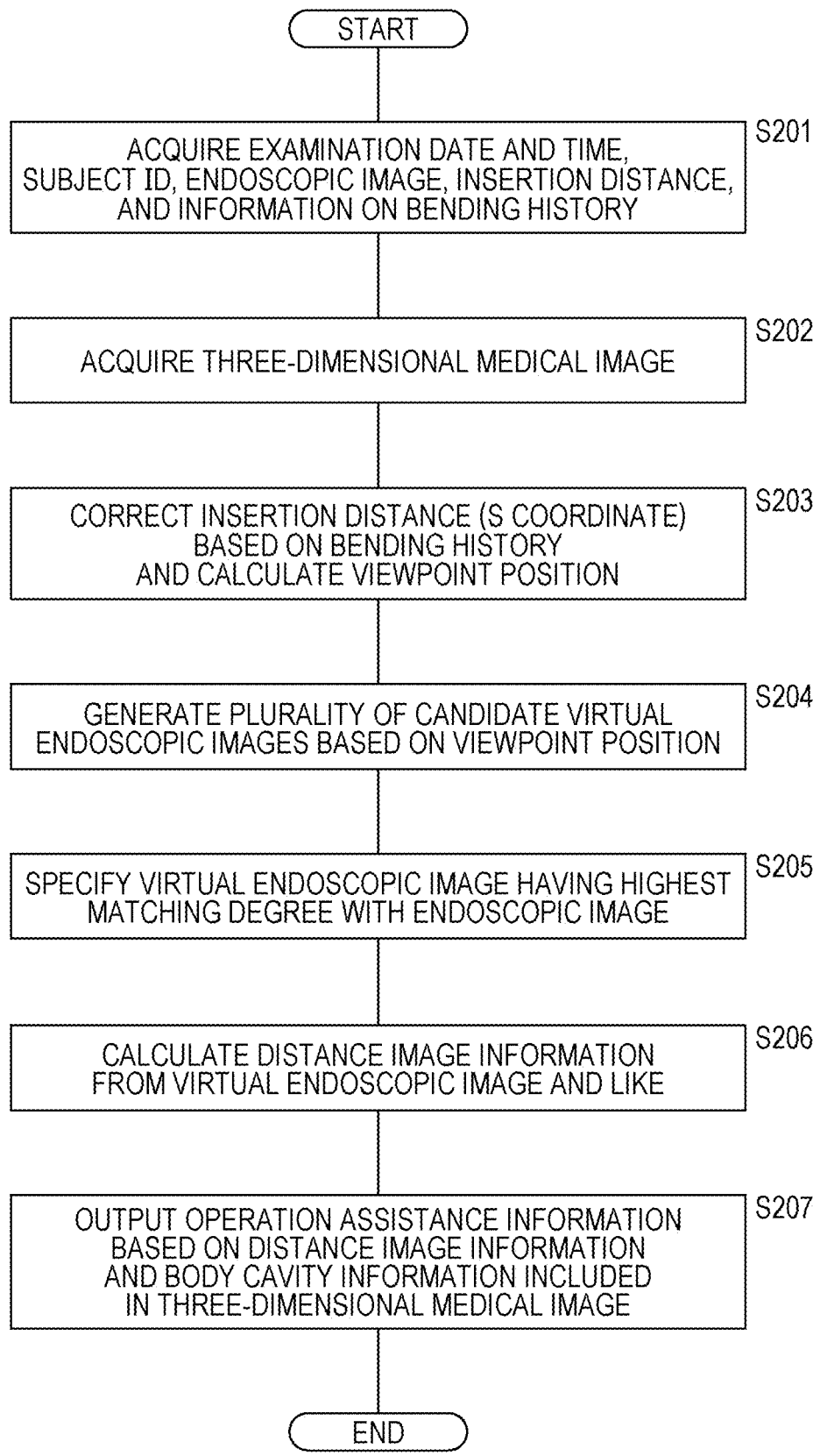
FIG. 13 is a flowchart illustrating an example of a processing procedure performed by the control unit of the information processing apparatus.

FIG. 13 is a flowchart illustrating an example of a processing procedure performed by the control unit of the information processing apparatus. For example, the information processing apparatus 6 starts processing of the flowchart based on contents input from the input unit 8 connected to the information processing apparatus 6.

The control unit 62 of the information processing apparatus 6 acquires the examination date and time, the subject ID, the endoscopic image, the insertion distance, and the information on the bending history which are output from the endoscope processor 20 (step S201). The control unit 62 of the information processing apparatus 6 acquires the endoscopic image from the endoscope processor 20 as in the first embodiment, and further acquires, for example, information on the bending history detected by an endoscope-insertion-shape observation device via the endoscope processor 20. Alternatively, the control unit 62 of the information processing apparatus 6 may directly acquire the information on the bending history from the endoscope-insertion-shape observation device.

The control unit 62 of the information processing apparatus 6 acquires a three-dimensional medical image which is output from an examination apparatus configured. to capture a three-dimensional image of the internal body, such as a CT apparatus, an MRI apparatus, or an ultrasonic diagnosis apparatus (step S202). The control unit 62 of the information processing apparatus 6 performs processing of step S202 similarly to processing of step S102 of the first embodiment.

The control unit 62 of the information processing apparatus 6 corrects the insertion distance (S coordinate) based on the bending history which is output from the endoscope processor 20, and calculates the viewpoint position (step S203). The control unit 62 calculates a shape of the insertion portion 44 (for example, rightward bending by 30 degrees) by arithmetic processing according to the bending angle and the bending direction included in the bending history, and recalculates (corrects) the S coordinate that is the insertion distance based on the calculated shape of the insertion portion 44. The control unit 62 calculates the viewpoint position based on the corrected insertion distance (S coordinate) as in the first embodiment.

The control unit 62 of the information processing apparatus 6 generates a plurality of candidate virtual endoscopic images based on the viewpoint position (step S204). The control unit 62 of the information processing apparatus 6 specifies a virtual endoscopic image having a highest matching degree with the endoscopic image among the plurality of generated virtual endoscopic images (step S205). The control unit 62 of the information processing apparatus 6 calculates distance image information from the acquired virtual endoscopic image (step S206). The control unit 62 of the information processing apparatus 6 outputs operation assistance information based on the distance image information and the body cavity information included in the three-dimensional medical image (step S207). The control unit 62 of the information processing apparatus 6 performs processing of step 204, step S205, step S206, and step S207 similarly to processing of step S104, step S105, step S106, and step S107 of the first embodiment.

According to the present embodiment, the coordinate information of the endoscope 40 and the information (viewpoint position) on the direction of the endoscope 40 in the coordinate system of the three-dimensional medical image are calculated based on the information on the shape of the endoscope 40, the information on the bending history, the information on the insertion distance, and the three-dimensional medical image. Therefore, it is possible to specify the position and the rotation angle (rotation angle in the x-axis, the y-axis, and the z-axis) of the endoscope 40 in the coordinate system of the three-dimensional medical image at the time of capturing the endoscopic image according to the shape of the endoscope 40. Thus, it is possible to accurately and efficiently calculate the distance image information in the endoscopic image based on the position and the rotation angle of the endoscope 40.

Third Embodiment

Figure 14:
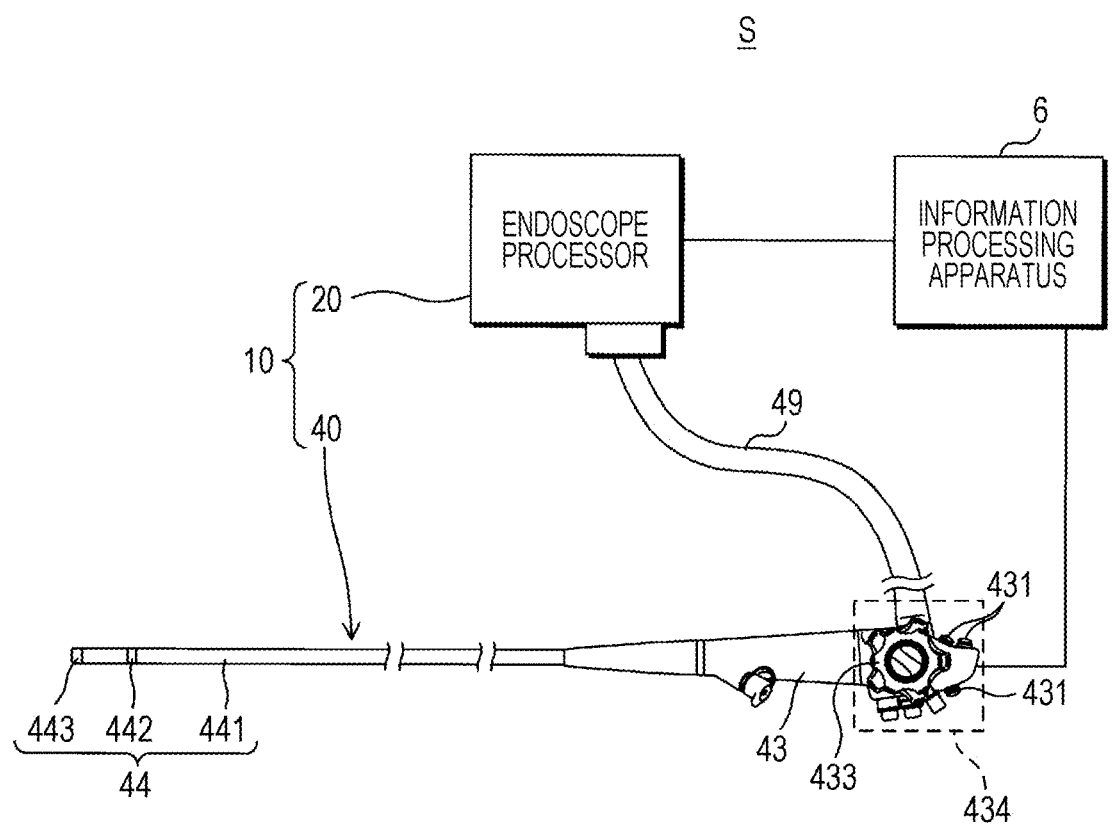
FIG. 14 is a schematic diagram illustrating an outline of a diagnosis assistance system according to a third embodiment (automatic operation mechanism).
Figure 15:
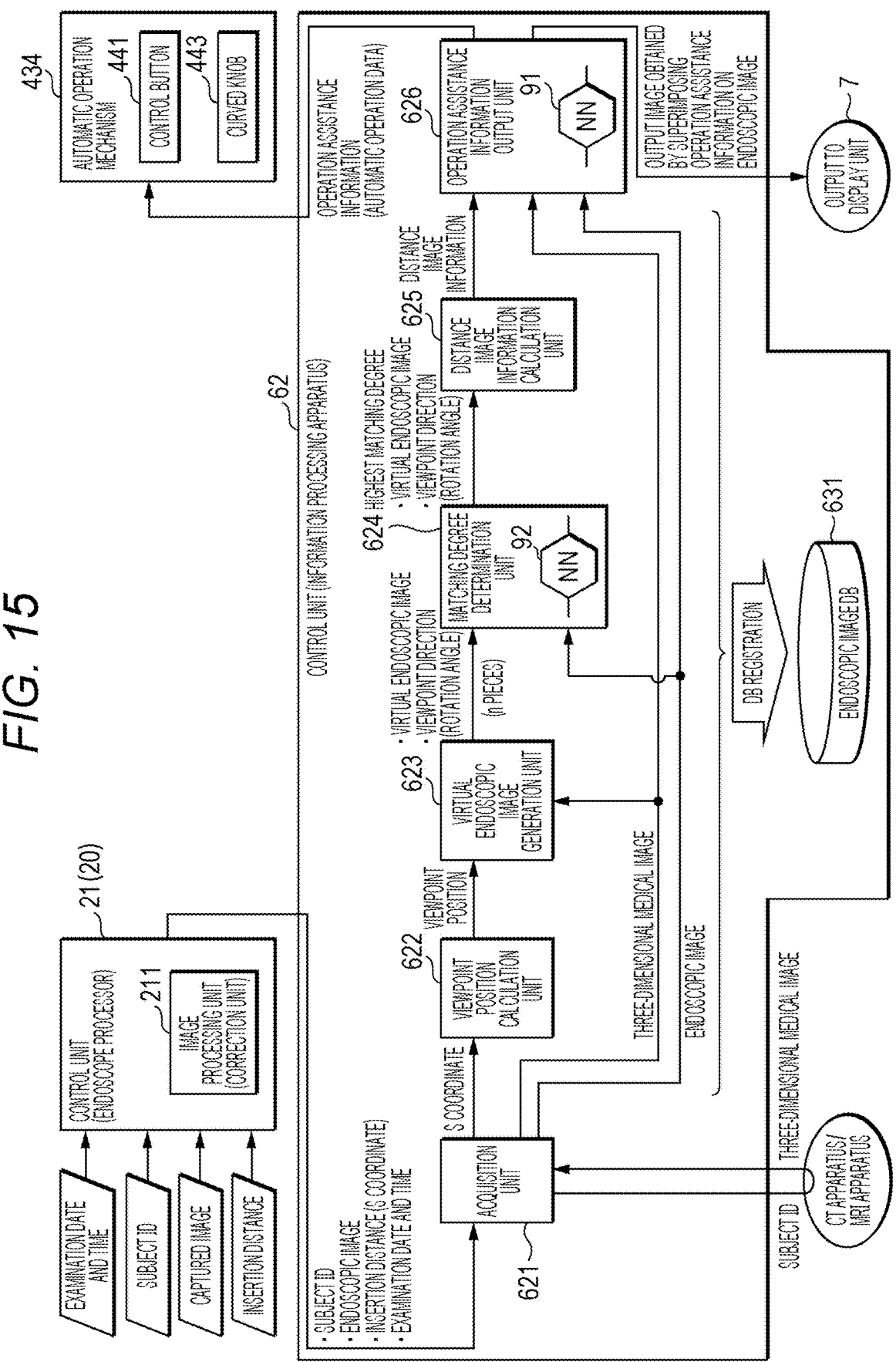
FIG. 15 is a functional block diagram exemplifying functional units included in the control unit of the information processing apparatus.

FIG. 14 is a schematic diagram illustrating an outline of the diagnosis assistance system S according to a third embodiment (automatic operation mechanism 434). FIG. 15 is a functional block diagram exemplifying functional units included in the control unit 62 of the information processing apparatus 6. The diagnosis assistance system S according to the third embodiment is different from the diagnosis assistance system according to the first embodiment in that the endoscope 40 included in the diagnosis assistance system S further includes an automatic operation mechanism 434.

The endoscope 40 included in the diagnosis assistance system S includes an automatic operation mechanism 434 that automatically operates the control button 431 and the bending knob 433 based on the operation assistance information output from the control unit 62 (operation assistance information output unit 626) of the information processing apparatus 6.

The automatic operation mechanism 434 is communicatively connected to the information processing apparatus 6, and acquires (receives) the operation assistance information which is output (transmitted) from the information processing apparatus 6. The automatic operation mechanism 434 includes, for example, a microcomputer (not illustrated) that generates an on/off signal or a pulse signal for the control button 431 or the bending knob 433 from the acquired operation assistance information, and a motor/cam mechanism (not illustrated) that operates or drives the control button 431 or the bending knob 433 based on the signal output from the microcomputer. In this manner, the automatic operation mechanism 434, the control button 431, and the bending knob 433 cooperate with each other based on the operation assistance information which is output from the information processing apparatus 6, and perform automatic operation such as automatic insertion of the endoscope 40 into the body of the subject according to the operation assistance information.

The operation assistance information that is acquired by the automatic operation mechanism 434 from the control unit 62 (operation assistance information output unit 626) of the information processing apparatus 6 is not limited to the operation assistance information such as insertion and bending of the insertion portion 44. For example, in a case where the insertion portion 44 of the endoscope 40 is provided with an air injection portion (not illustrated) or a hand portion (not illustrated), the operation assistance information may include information on an operation such as injection of air by using the air injection portion or extraction (sampling) of a lesion part by using the hand portion. That is, the operation assistance information output unit 626 generates information on an operation of the air injection portion or the hand portion based on the shape information and the distance image information of the internal body part specified in the acquired three-dimensional medical image, includes the information in the operation assistance information, and outputs the operation assistance information to the automatic operation mechanism 434. The automatic operation mechanism 434 may automatically operate the air injection portion or the hand portion based on the acquired operation assistance information. The information on the operation of the air injection portion or the hand portion included in the operation assistance information may be displayed on the integrated image display screen 71 by being superimposed on the endoscopic image.

According to the present embodiment, based on the distance image information in the endoscopic image, and the three-dimensional medical image or the virtual endoscopic image, it is possible to efficiently output the operation assistance information on the operation of the endoscope 40. Thus, the automatic operation mechanism 434 automatically operates the endoscope 40 according to the operation assistance information which is output from the endoscope processor 20. Therefore, it is possible to provide, for an operator who operates the endoscope 40 such as a doctor, the diagnosis assistance system S that efficiently assists an operation of the endoscope 40.

The embodiments herein are disclosed for purposes of illustration in all respects without being limited. The technical features described in the respective embodiments can be combined with each other, and the scope of the present invention is intended to include all modifications within the scope of the claims and the scope equivalent to the claims.

REFERENCE SIGNS LIST

S Diagnosis assistance system
10 Endoscope apparatus
15 Keyboard
16 Storage shelf
20 Endoscope processor
21 Control unit
211 Image processing unit
22 Main storage device
23 Auxiliary storage device
24 Communication unit
25 Touch panel
26 Display device IN
27 Input device OF
28 Reading unit
31 Endoscope connector
311 Electrical connector
312 Optical connector
33 Light source
34 Pump
35 Water supply tank
36 Air supply/water supply port
40 Endoscope
43 Operation unit
431 Control button
433 Bending knob
434 Automatic operation mechanism
44 Insertion portion (flexible tube)
441 Soft portion
442 Bending portion
443 Distal end portion
444 Imaging unit 446 Imaging light source
45 Bend preventing portion
48 Scope connector
49 Universal cord
50 Display device
6 Information processing apparatus
61 Communication unit
62 Control unit
621 Acquisition unit
622 Viewpoint position calculation unit
623 Virtual endoscopic image generation unit
624 Matching degree determination unit
625 Distance image information calculation unit
626 Operation assistance information output unit
63 Storage unit
631 Endoscopic image DB
632 Recording medium
P Program
64 Input/output I/F
7 Display unit
71 Integrated image display screen.
711 Display option field
712 Display mode selection field
8 Input unit
91 Operation information learning model
92 Matching degree learning model

The invention claimed is:

1. A non-transitory computer-readable medium containing a program causing a computer to execute processing comprising:
    acquiring an endoscopic image of a subject from an endoscope;
    acquiring a three-dimensional medical image obtained by capturing an image of an internal body portion of the subject by means of X-ray CT, X-ray cone beam CT, MRI-CT, or an ultrasonic diagnosis apparatus configured to capture a three-dimensional image of an internal body portion of the subject;
    generating a virtual endoscopic image reconfigured from the three-dimensional medical image, based on the acquired endoscopic image;
    calculating distance image information in the endoscopic image based on the virtual endoscopic image and the endoscopic image; and
    outputting operation assistance information on an operation of the endoscope based on the distance image information and the three-dimensional medical image, wherein
    the operation assistance information includes an insertion speed of the endoscope.

2. The non-transitory computer-readable medium containing a program according to claim 1, wherein
    the operation assistance information includes information on an insertion direction and an insertion distance of the endoscope is output based on the distance image information and the three-dimensional medical image.

3. The non-transitory computer-readable medium containing a program according to claim 1, wherein the distance image information including information on a size of an internal body part included in the endoscopic image or a distance between the internal body parts is calculated based on the virtual endoscopic image and the endoscopic image.

4. The non-transitory computer-readable medium containing a program according to claim 1, wherein
    information on an insertion distance of the endoscope inserted into the internal body portion of the subject is acquired,
    coordinate information of the endoscope in a coordinate system of the three-dimensional medical image is calculated based on the information on the insertion distance and the three-dimensional medical image, and
    the operation assistance information on an operation of the endoscope is output based on the coordinate information of the endoscope, the distance image information, and the three-dimensional medical image.

5. The non-transitory computer-readable medium containing a program according to claim 4, wherein
    information on a bending history of the endoscope inserted into the internal body portion of the subject is acquired,
    coordinate information of the endoscope and information on a direction of the endoscope in a coordinate system of the three-dimensional medical image are calculated based on the information on the bending history, the information on the insertion distance, and the three-dimensional medical image, and
    the operation assistance information on an operation of the endoscope is output based on the coordinate information of the endoscope, the distance image information, and the three-dimensional medical image.

6. The non-transitory computer-readable medium containing a program according to claim 5, wherein
    information on a shape of the endoscope is acquired,
    coordinate information of the endoscope and information on a direction of the endoscope in a coordinate system of the three-dimensional medical image are calculated based on the information on the shape of the endoscope, the information on the bending history, the information on the insertion distance, and the three-dimensional medical image, and
    the operation assistance information on an operation of the endoscope is output based on the coordinate information of the endoscope, the information on the direction of the endoscope, the virtual endoscopic image, and the endoscopic image.

7. The non-transitory computer-readable medium containing a program according to claim 1, wherein the generating of the virtual endoscopic image includes a process of
    generating a two-dimensional medical image obtained by projecting the three-dimensional medical image, and
    setting, in the generated two-dimensional medical image, as the virtual endoscopic image, a two-dimensional medical image in which a difference from the endoscopic image is equal to or smaller than a predetermined value.

8. The non-transitory computer-readable medium containing a program according to claim 1, wherein the generating of the virtual endoscopic image includes a process of
    generating a two-dimensional medical image obtained by projecting the three-dimensional medical image,
    inputting the two-dimensional medical image and the endoscopic image to a learning model, which is learned so as to output a matching degree between the two-dimensional medical image and the endoscopic image, in a case where the two-dimensional medical image and the endoscopic image are input,
    acquiring a matching degree between the two-dimensional medical image and the endoscopic image from the learning model, and
    setting, as the virtual endoscopic image, the two-dimensional medical image in which the matching degree between the two-dimensional medical image and the endoscopic image is equal to or higher than a predetermined value.

9. An information processing method causing a computer to execute processing comprising:
- acquiring an endoscopic image of a subject from an endoscope;
- acquiring a three-dimensional medical image obtained by capturing an image of an internal body portion of the subject by means of X-ray CT, X-ray cone beam CT, MRI-CT, or an ultrasonic diagnosis apparatus configured to capture a three-dimensional image of an internal body portion of the subject;
- generating a virtual endoscopic image reconfigured from the three-dimensional medical image, based on the acquired endoscopic image;
- calculating distance image information in the endoscopic image based on the virtual endoscopic image and the endoscopic image; and
- outputting operation assistance information on an operation of the endoscope based on the distance image information and the three-dimensional medical image, wherein
- the operation assistance information includes an insertion speed of the endoscope.

10. An information processing apparatus comprising:
- an image sensor that acquires an endoscopic image of a subject from an endoscope;
- an X-ray CT, an X-ray cone beam CT, an MRI-CT, or an ultrasonic diagnosis apparatus that acquires a three-dimensional medical image of an internal body portion of the subject by capturing an image of the internal body portion of the subject; and
- a processor that generates a virtual endoscopic image reconfigured from the three-dimensional medical image, based on the acquired endoscopic image, wherein the processor also
  - calculates distance image information in the endoscopic image based on the virtual endoscopic image and the endoscopic image; and
  - outputs operation assistance information on an operation of the endoscope based on the distance image information and the three-dimensional medical image, wherein
- the operation assistance information includes an insertion speed of the endoscope.

\* \* \* \* \*